(12) United States Patent
Macht et al.

(10) Patent No.: US 8,686,194 B2
(45) Date of Patent: Apr. 1, 2014

(54) MO-, BI- AND FE-COMPRISING MULTIMETAL OXIDE COMPOSITIONS

(75) Inventors: Josef Macht, Mannheim (DE); Andrey Karpov, Metuchen, NJ (US); Cornelia Katharina Dobner, Ludwigshafen (DE); Frank Rosowski, Mannheim (DE); Ulrich Hammon, Mannheim (DE); Klaus Joachim Müller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/546,546

(22) Filed: Jul. 11, 2012

(65) Prior Publication Data

US 2013/0023699 A1    Jan. 24, 2013

Related U.S. Application Data

(60) Provisional application No. 61/506,693, filed on Jul. 12, 2011, provisional application No. 61/543,333, filed on Oct. 5, 2011.

(30) Foreign Application Priority Data

Jul. 12, 2011 (DE) .......................... 10 2011 079 035
Oct. 5, 2011 (DE) .......................... 10 2011 084 040

(51) Int. Cl.
C07C 45/28 (2006.01)
B01J 23/887 (2006.01)

(52) U.S. Cl.
USPC ............ 568/449; 502/243; 502/249; 502/311

(58) Field of Classification Search
USPC ............................ 568/449; 502/243, 249, 311
See application file for complete search history.

(56) References Cited

U.S. PATENT DOCUMENTS

| | | | |
|---|---|---|---|
| 2005/0131253 A1 | 6/2005 | Teshigahara et al. | |
| 2008/0171897 A1 | 7/2008 | Raichle et al. | |
| 2011/0077148 A1 | 3/2011 | Kano et al. | |

FOREIGN PATENT DOCUMENTS

| | | |
|---|---|---|
| DE | 29 09 671 A1 | 10/1980 |
| DE | 44 07 020 A1 | 9/1994 |
| DE | 44 31 957 A1 | 3/1995 |
| DE | 44 42 346 A1 | 5/1996 |
| DE | 198 55 913 A1 | 6/2000 |
| DE | 199 10 506 A1 | 9/2000 |
| DE | 199 48 248 A1 | 4/2001 |
| DE | 199 48 523 A1 | 4/2001 |
| DE | 100 46 957 A1 | 4/2002 |
| DE | 100 49 873 A1 | 4/2002 |
| DE | 100 59 713 A1 | 6/2002 |
| DE | 100 63 162 A1 | 6/2002 |
| DE | 102 32 748 | 7/2002 |
| DE | 103 13 209 A1 | 3/2004 |
| DE | 102 45 585 A1 | 4/2004 |
| DE | 102 46 119 A1 | 4/2004 |
| DE | 103 13 208 A1 | 10/2004 |
| DE | 103 13 213 A1 | 10/2004 |
| DE | 103 37 788 A1 | 10/2004 |
| DE | 10 2005 037 678 A1 | 2/2007 |
| DE | 10 2006 044 520 A1 | 4/2008 |
| DE | 10 2007 005 606 A1 | 4/2008 |
| DE | 10 2007 003 076 A1 | 7/2008 |
| DE | 10 2007 004 961 A1 | 7/2008 |
| DE | 10 2008 040 093 A1 | 12/2008 |
| DE | 10 2008 040 094 A1 | 1/2009 |
| DE | 10 2008 042 060 A1 | 6/2009 |
| DE | 10 2008 042 061 A1 | 3/2010 |
| DE | 10 2008 042 064 A1 | 3/2010 |
| DE | 10 2008 054 586 A1 | 6/2010 |
| DE | 10 2009 047 291 A1 | 9/2010 |
| DE | 10 2010 048 405 A1 | 5/2011 |
| EP | 0 184 790 A2 | 6/1986 |
| EP | 0 293 859 A1 | 12/1988 |
| EP | 0 575 897 A1 | 12/1993 |
| EP | 0 468 290 B1 | 3/1994 |
| EP | 0 700 714 A1 | 3/1996 |
| EP | 0 700 893 A1 | 3/1996 |
| EP | 0 714 700 A2 | 6/1996 |
| EP | 0 873 783 A1 | 10/1998 |
| EP | 0 990 636 A1 | 4/2000 |
| EP | 1 106 598 A2 | 6/2001 |
| EP | 1 525 178 | 1/2004 |
| WO | 00/53557 | 9/2000 |
| WO | 00/53558 | 9/2000 |
| WO | 01/36364 A1 | 5/2001 |
| WO | 02/24620 A2 | 3/2002 |
| WO | 02/49757 A2 | 6/2002 |
| WO | 02/062737 A2 | 8/2002 |
| WO | 2005/030393 A1 | 4/2005 |
| WO | 2005/042459 A1 | 5/2005 |
| WO | 2005/047224 A1 | 5/2005 |
| WO | 2005/113127 A1 | 12/2005 |
| WO | 2006/042459 A1 | 4/2006 |
| WO | 2007/017431 A1 | 2/2007 |
| WO | 2007/082827 A1 | 7/2007 |
| WO | 2008/087116 A1 | 7/2008 |
| WO | 2010/066645 A2 | 6/2010 |

OTHER PUBLICATIONS

International Search Report issued Sep. 27, 2012 in Application No. PCT/EP2012/063530 (With English translation of category of cited documents).

*Primary Examiner* — Sikarl Witherspoon
(74) *Attorney, Agent, or Firm* — Oblon, Spivak, McClelland, Maier & Neustadt, L.L.P.

(57) ABSTRACT

Mo-, Bi- and Fe-comprising multimetal oxide compositions of the general stoichiometry I, $$Mo_{12}Bi_aCo_bFe_cK_dSi_eO_x \qquad (I),$$

where
a=0.5 to 1,
b=7 to 8.5,
c=1.5 to 3.0,
d=0 to 0.15,
e=0 to 2.5 and
x=the stoichiometric coefficient of $O^{2-}$ which guarantees the electric neutrality of the multimetal oxide,
and $$12-b-1.5 \cdot c = A \text{ and } 0.5 \leq A \leq 1.5,$$

$$0.2 \leq a/A \leq 1.3, \text{ and}$$

$$2.5 \leq b/c \leq 9,$$

and the use thereof.

14 Claims, 6 Drawing Sheets

MO-, BI- AND FE-COMPRISING MULTIMETAL OXIDE COMPOSITIONS

The present invention relates to Mo-, Bi- and Fe-comprising multimetal oxide compositions of the general stoichiometry I, $$Mo_{12}Bi_aCo_bFe_cK_dSi_eO_x \qquad (I),$$

where the variables have the following meanings:
a=0.5 to 1,
b=7 to 8.5,
c=1.5 to 3.0,
d=0 to 0.15,
e=0 to 2.5 and
x=a number which is determined by the valence and abundance of the elements other than oxygen in I
and fulfill the following conditions:

$$12-b-1.5 \cdot c = A,$$

and $0.5 \leq A \leq 1.5;$      condition 1

$0.2 \leq a/A \leq 1.3;$ and      condition 2

$2.5 \leq b/c \leq 9.$      condition 3

In addition, the present invention relates to a process for preparing multimetal oxide compositions of the general stoichiometry I and to their use as catalytically active compositions of catalysts for the heterogeneously catalyzed partial gas-phase oxidation of organic compounds, in particular that of propene to form acrolein as main product and acrylic acid as by-product.

Mo-, Bi- and Fe-comprising multimetal oxide compositions of the general stoichiometry I which do not fulfill the conditions 1, 2 and 3 are, for example, known from DE-A 19855913.

The use of such multimetal oxide compositions as active compositions of catalysts for the heterogeneously catalyzed partial gas-phase oxidation of propene to acrolein as main product and acrylic acid as desirable by-product (acrylic acid is therefore a particularly desirable by-product because the heterogeneously catalyzed partial gas-phase oxidation of propene to acrolein is, in particular, employed as first oxidation stage of the two-stage partial oxidation of propene to acrylic acid) is also known from DE-A 19855913.

However, a disadvantage of the multimetal oxide compositions of DE-A 19855913 as active compositions of catalysts for the heterogeneously catalyzed partial gas-phase oxidation of propene to form acrolein as main product and acrylic acid as desirable by-product is, in particular, that the resulting total selectivity for the formation of acrolein and acrylic acid is not fully satisfactory.

What has been said in respect of the multimetal oxide compositions of DE-A 19855913 also applies to the Mo-, Bi- and Fe-comprising multimetal oxide compositions of DE-A 10063162, DE-A 102005037678, DE-A 10059713, DE-A 10049873, DE-A 102007003076, DE-A 102008054586, DE-A 102007005606 and DE-A 102007004961.

It is therefore, in particular, an object of the present invention to provide Mo-, Bi- and Fe-comprising multimetal oxide compositions which, as active compositions of catalysts for the heterogeneously catalyzed partial gas-phase oxidation of propene to form acrolein as main product and acrylic acid as by-product make possible an improved total selectivity for the formation of acrolein and acrylic acid (i.e. an improved total selectivity to product of value).

The object is achieved by the provision of Mo-, Bi- and Fe-comprising multimetal oxide compositions of the general stoichiometry I, $$Mo_{12}Bi_aCo_bFe_cK_dSi_eO_x \qquad (I),$$

where the variables have the following meanings:
a=0.5 to 1,
b=7 to 8.5,
c=1.5 to 3.0,
d=0 to 0.15,
e=0 to 2.5 and
x=a number which is determined by the valence and abundance of the elements other than oxygen in I
and fulfill the following conditions:

$$12-b-1.5 \cdot c = A,$$

and $0.5 \leq A \leq 1.5;$      condition 1

$0.2 \leq a/A \leq 1.3;$ and      condition 2

$2.5 \leq b/c \leq 9.$      condition 3

According to the invention, the stoichiometric coefficient d is preferably from 0.04 to 0.1 and particularly preferably from 0.05 to 0.08.

The stoichiometric coefficient e is, according to the invention, advantageously from 0.5 to 2 and particularly advantageously from 0.8 to 1.8 or from 1 to 1.6.

Furthermore, in respect of condition 1, $0.5 \leq A \leq 1.25$ is advantageous and $0.5 \leq A \leq 1$ is particularly advantageous.

In respect of condition 2, preference is given according to the invention to $0.3 \leq a/A \leq 1.2$, particularly preferably $0.4 \leq a/A \leq 1.2$ and very particularly preferably $0.5 \leq a/A \leq 1$.

The ratio b:c=b/c (condition 3) advantageously fulfills, according to the invention, the relationship $3 \leq b/c \leq 9$, particularly advantageously the relationship $3 \leq b/c \leq 7$ and very particularly advantageously the relationship $3 \leq b/c \leq 5$.

Very particularly preferred multimetal oxide compositions of the general stoichiometry I are thus those in which, simultaneously:
d=0.04 to 0.1;
e=0.5 to 2;
$0.5 \leq A \leq 1.25$;
$0.4 \leq a/A \leq 1.2$; and
$3 \leq b/c \leq 9$.

Alternatively, very particularly preferred multimetal oxide compositions of the general stoichiometry I are those in which, simultaneously:
d=0.04 to 0.1;
e=0.8 to 1.8;
$0.5 \leq A \leq 1$;
$0.5 \leq a/A \leq 1.2$; and
$3 \leq b/c \leq 5$.

Figure 1:
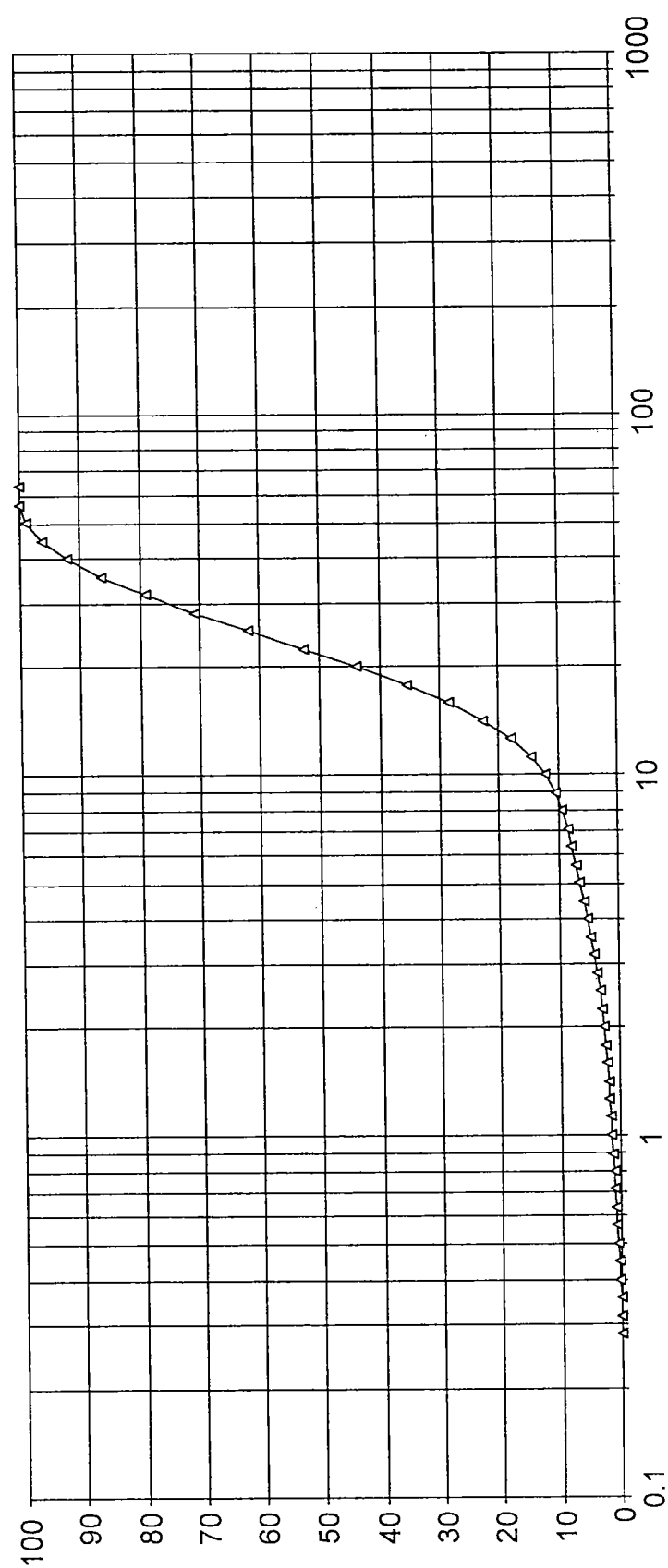
FIG. 1 shows a representative particle diameter distribution of spray-dried powder (dispersion pressure=2 bar absolute) with $d_{10}=9$ μm, $d_{50}=22$ μm and $d_{90}=39$ μm.

Multimetal oxide compositions according to the invention of the general stoichiometry I are usually used as such (known as all-active catalysts) shaped into geometric shaped bodies such as spheres, rings or (solid) cylinders or in the form of coated catalysts, i.e. prefabricated inert (shaped) support bodies coated with the multimetal oxide (active) composition for catalyzing the respective heterogeneously catalyzed gas-phase partial oxidation (e.g. of propene to acrolein). Of course, they can also be used in powder form as catalysts for such catalysis.

Multimetal oxide (active) compositions of the general stoichiometry I can in principle be prepared in a simple way by producing a very intimate, preferably finely divided, dry mix having a composition corresponding to the respective stoichiometry from suitable sources of their elemental constituents (in particular those other than oxygen) and calcining this, if desired after previous shaping to give shaped bodies having a regular or irregular geometry, if desired with concomitant use of shaping aids, at temperatures in the range from 350 to 650° C. The calcination can be carried out either under inert gas or under an oxidizing atmosphere such as air (or another mixture of inert gas and molecular oxygen) or else under a reducing atmosphere (e.g. a mixture of inert gas, $NH_3$, CO and/or $H_2$) or under reduced pressure. The calcination time can be from a few minutes to some hours and usually decreases with increasing calcination temperature.

Possible sources of the elemental constituents of the multimetal oxide compositions of the general stoichiometry I (the multimetal oxide active compositions I) are compounds which are already oxides and/or compounds which can be converted into oxides by heating, at least in the presence of oxygen.

Apart from the oxides, possible starting compounds (sources) of this type are, in particular, halides, nitrates, formates, oxalates, citrates, acetates, carbonates, amine complexes, ammonium salts and/or hydroxides and also hydrates of the abovementioned salts. Compounds such as $NH_4OH$, $(NH_4)CO_3$, $NH_4NO_3$, $NH_4CHO_2$, $CH_3COOH$, $NH_4CH_3CO_2$ and/or ammonium oxalate which later decompose and/or can be decomposed into gaseous compounds which are given off at the latest during the later calcination can be additionally incorporated into the intimate dry mix. Possible substances of this type which decompose during calcination also include organic materials such as stearic acid, malonic acid, ammonium salts of the abovementioned acids, starches (e.g. potato starch and maize starch), cellulose, ground nut shells and finely divided ground plastic (e.g. polyethylene, polypropylene, etc.).

The intimate mixing of the starting compounds (sources) for preparing multimetal oxide active compositions I can be carried out dry or wet. If it is carried out dry, the starting compounds (the sources) are advantageously used as fine powders and after mixing and optionally compaction to form geometric shaped precursor bodies are subjected to calcination. However, intimate mixing is preferably carried out wet.

According to the invention, the starting compounds are in this case advantageously mixed with one another in the form of solutions and/or suspensions and the resulting wet mixture M is subsequently dried to give the intimate dry mix. Preference is given to using water or an aqueous solution as solvent and/or suspension medium.

Very particularly intimate dry mixes are obtained in the above-described mixing process when sources present in dissolved form and/or colloidally dissolved sources of the elemental constituents are exclusively used as starting materials. A starting compound can quite generally be a source of only one elemental constituent or of more than one elemental constituent. Analogously, an above-described solution or colloidal solution can have only one elemental constituent or more than one elemental constituent in dissolved form. A preferred solvent here is, as indicated above, water. Drying of the resulting aqueous mixtures is preferably effected by spray drying.

When mention is made in the present text of a solution of a source (starting compound, starting substance) in a solvent (e.g. water), the term "dissolution" is meant in the sense of a molecular or ionic solution. This means that the largest geometric unit of the dissolved starting substance (source) present in the solution must have "molecular" dimensions.

In comparison, colloidal solutions are a link between genuine (molecular and/or ionic) solutions and suspensions. These colloidally disperse systems comprise relatively small accumulations of molecules or atoms which can, however, not be discerned either with the naked eye or by means of a microscope. The colloidal solution visually appears completely clear (even though often colored) since the particles comprised therein have a diameter of only from 1 to 250 nm, (preferably up to 150 nm and particularly preferably up to 100 nm). Owing to the small size, the colloidally dissolved particles cannot be separated off by conventional filtration. However, they can be separated off from their "solvent" by ultrafiltration using membranes of vegetable, animal or synthetic origin (e.g. parchment, pig's bladder or cellophane). In contrast to the "optically empty" genuine (molecular and/or ionic) solutions, a light ray cannot pass through a colloidal solution without deflection. The light ray is scattered and deflected by the colloidally dissolved particles. To keep colloidal solutions stable and prevent further particle agglomeration, they frequently comprise wetting agents and dispersants and also other additives.

For example, the element silicon (the elemental constituent Si) can be introduced in the form of a silica sol to produce the wet (e.g. aqueous) mixture M. Silica sols are colloidal solutions of amorphous silicon dioxide in water. They are fluid like water and do not comprise any sedimentable constituents. Their $SiO_2$ content can often be up to 50% by weight and more while often keeping for years (without sedimentation).

Of course, molecularly and/or ionically dissolved sources and colloidally dissolved sources can also be present side by side in solution in a solution of at least one element source to be used for producing a wet (e.g. aqueous) mixture M.

An advantageous Mo source for the preparation of multimetal oxide active compositions I according to the invention is ammonium heptamolybdate tetrahydrate. Further possible Mo sources are ammonium orthomolybdate (($NH_4)_2MoO_4$), ammonium dimolybdate (($NH_4)_2Mo_2O_7$), ammonium tetramolybdate dihydrate (($NH_4)_2Mo_4O_{13} \times 5H_2O$) and ammonium decamolybdate dihydrate (($NH_4)_4Mo_{10}O_{32} \times 2H_2O$). However, it is in principle also possible to use, for example, molybdenum trioxide.

A preferred K source for preparing multimetal oxide compositions I according to the invention is KOH (potassium hydroxide). However, it is in principle also possible to use $KNO_3$ or the hydrate thereof as K source.

As Bi source for preparing multimetal oxide active compositions I according to the invention, preference is given to using salts of bismuth having the Bi present as $Bi^{3+}$. Possible salts of this type are, for example, bismuth(III) oxide, bismuth (III) oxide nitrate (bismuth subnitrate), bismuth(III) halide (e.g. fluoride, chloride, bromide, iodide) and in particular bismuth(III) nitrate pentahydrate.

Fe sources which are preferred according to the invention are salts of $Fe^{3+}$, among which the various iron(III) nitrate hydrates are particularly preferred (cf., for example, DE-A 102007003076). Particular preference is given according to the invention to using iron(III) nitrate nonahydrate as Fe source. Of course, it is also possible to use salts of $Fe^{2+}$ as Fe source in a preparation according to the invention of multimetal oxide active compositions I.

It is advantageous, according to the invention, to introduce at least 50 mol %, better at least 75 mol % and preferably at least 95 mol %, of the total molar amount of Fe comprised in multimetal oxide compositions I according to the invention in the form of an Fe source in which the Fe is present as $Fe^{3+}$ for preparing these multimetal oxide compositions I. It is also possible to use sources which comprise both $Fe^{2+}$ and $Fe^{3+}$.

Co sources which are suitable according to the invention are salts of Co in which the Co is present as $Co^{2+}$ and/or $Co^{3+}$. Examples which may be mentioned are cobalt(II) nitrate hexahydrate, $Co_3O_4$, CoO, cobalt(II) formate and cobalt(III) nitrate. The first of these sources is particularly preferred.

Frequently, the production of a wet (e.g. aqueous) mixture M is, according to the invention, preferably carried out in air (the aqueous mixture M is advantageously saturated with air). This applies particularly when salts of $Co^{2+}$ and salts of $Fe^{2+}$ are used as cobalt and iron sources, especially when these salts are the nitrates and/or hydrates thereof. Said salts are advantageous not least because $Fe^{2+}$ and $Co^{2+}$ can be oxidized at least partially to $Fe^{3+}$ and $Co^{3+}$ by the molecular oxygen of air in the presence of $NO_3^-$.

As mentioned above, the wet mixture M is, according to the invention, preferably an aqueous mixture M which is particularly advantageously produced in the following way. An aqueous solution A having a pH of ≤3, preferably ≤2, particularly preferably ≤1 and very particularly preferably ≤0, is produced from at least one source of the elements Co, Fe and Bi. In general, the pH of the aqueous solution A is not less than −2 and particularly advantageously in the range from −1 to 0. The aqueous solution A is preferably an aqueous solution of the nitrates or nitrate hydrates of Co, Bi and Fe. The aqueous solution A is particularly preferably an aqueous solution of the nitrates or nitrate hydrates in aqueous nitric acid. To produce such a solution, solutions of the relevant elements in aqueous nitric acid can also be used directly as element source.

An aqueous solution B is produced from at least one source of the element Mo and if desired one or more sources of the element K. The pH of the aqueous solution B is, according to the invention, advantageously (at 25° C. and 1.01 bar)<7. The pH of the aqueous solution B is particularly preferably ≤6.5 and very particularly advantageously ≤6. In general, the pH of the aqueous solution B will be ≥3. Advantageous solutions B to be used according to the invention have a pH of from 4 to 6. pH values of aqueous solutions are, for the purposes of the present text, generally (unless explicitly indicated otherwise) based on a measurement at 25° C. and 1 atm (1.01 bar) using a combination glass electrode. This is calibrated by means of buffer solutions whose pH is known and is in the vicinity of the expected measured value. The Mettler Toledo pH electrode Inpro 4260/425/Pt 100, which is a combination electrode with integrated Pt 100 temperature sensor for automatic temperature compensation, is particularly suitable for determining pH values in the context of the invention.

If the aqueous solution B comprises K, KOH is advantageously used as K source for preparing the aqueous solution B. A preferred Mo source for preparing an aqueous solution B is ammonium heptamolybdate tetrahydrate $((NH_4)_6Mo_7O_{24} \times 4H_2O)$.

The total Co, Fe and Bi content of the aqueous solution is, according to the invention, advantageously from 10 to 25% by weight, more advantageously from 15 to 20% by weight, based on the amount of water comprised in the aqueous solution A.

The total Mo content of the aqueous solution B is, according to the invention, advantageously from 3 to 25% by weight, more advantageously from 5 to 15% by weight, based on the amount of water comprised in the aqueous solution B.

The aqueous solution A and the aqueous solution B are then advantageously mixed with one another. According to the invention, it is advantageous to stir the aqueous solution A continuously into the aqueous solution B. According to the invention, the initially charged aqueous solution B is advantageously stirred intensively. The total Mo, Co, Fe and Bi content of the resulting aqueous mixture of aqueous solution A and aqueous solution B is, according to the invention, advantageously from 5 to 25% by weight, more advantageously from 8 to 20% by weight, based on the amount of water comprised in the aqueous mixture.

The temperature of the initially charged aqueous solution B and of the intensively stirred aqueous mixture resulting from the stirring of the aqueous solution A into the aqueous solution B is, according to the invention, advantageously (preferably during the entire mixing process) ≤80° C., better ≤70° C., even better ≤60° C. and preferably ≤40° C. In general, the abovementioned temperature will not go below 0° C. The aqueous solution A stirred into the solution B advantageously has the same temperature as the initially charged solution B. The temperature of the aqueous initial charge is preferably constant over the course of the stirring-in process described. For this purpose, the solution can, for example, be thermostatted by means of a waterbath. The working pressure is advantageously 1.01 bar (1 atm).

The aqueous solution A is preferably stirred into the initially charged aqueous solution B over a period in the range from 5 to 60 minutes, particularly preferably over a period of from 10 to 30 minutes and very particularly preferably over a period of from 15 to 25 minutes. The resulting aqueous mixture is subsequently advantageously stirred further, preferably while maintaining the stirring-in temperature, for from 5 to 60 minutes, advantageously from 10 to 30 minutes and particularly advantageously from 15 to 25 minutes.

The magnitude of the period of time over which the aqueous solution A and the aqueous solution B are combined has essentially no influence on the selectivity of the multimetal oxide active composition I produced in the further course of the process. Excessively long stirring after combination (≥4 h) reduces the selectivity. It has also been found that the magnitude of the abovementioned periods of time has a certain influence on the activity of the multimetal oxide active composition I produced in the further course of the process. Thus, relatively slow stirring of the aqueous solution A into the aqueous solution B increases the activity, while too rapid stirring of the aqueous solution A into the aqueous solution B reduces the activity. The latter also applies to excessive further stirring (e.g. ≥3 h, or ≥4 h).

The ratio V of the total molar amount $n_1$ of $NH_3$ and $NH_4^+$ present if desired in the aqueous mixture of the aqueous solution A and the aqueous solution B to the total molar amount $n_2$ of Mo comprised in the same aqueous mixture ($V = n_1 : n_2$) is, according to the invention, advantageously set so that V≤1.5, preferably ≤1 and particularly preferably ≤6/7. V can in principle also be 0. The pH of the aqueous mixture of aqueous solution A and aqueous solution B is advantageously at the same time ≤3, better ≤2. In general, it is ≥0.

If the desired multimetal oxide active composition I comprises the elemental constituent Si, aqueous silica sol (cf., for example, DE-A 102006044520) is advantageously used as source thereof and is advantageously stirred into the aqueous mixture of aqueous solution A and aqueous solution B, with water advantageously being able to be additionally added to this aqueous mixture before this stirring-in. It can be advantageous to add both the aqueous silica sol and the water all at once. Both the temperature of the water and the temperature of the aqueous silica sol advantageously correspond here to the temperature of the aqueous mixture of aqueous solution A and aqueous solution B. Finally, the mixture is advantageously stirred further for up to 30 minutes. During the further stirring, the abovementioned temperature is advantageously maintained. The $SiO_2$ content of the added aqueous silica sol can be from 15 to 60% by weight or from 20 to 60% by weight or from 30 to 60% by weight, advantageously from 40 to 60% by weight and particularly preferably from 45 to 55% by weight (in each case based on the total weight thereof).

Instead of placing the aqueous solution B in a thermostatted stirred vessel and subsequently allowing the aqueous solution A to run into it while stirring, it is also possible to introduce both the aqueous solution B and the aqueous solution A continuously into the stirred vessel (e.g. through a "3-way T-mixer"). The aqueous solution B can in principle also be stirred continuously into an initially charged aqueous solution A. However, this procedure is less preferred according to the invention.

In an alternative embodiment, an aqueous solution A* is produced from sources of the elements Fe and Bi. An aqueous solution B* is produced from sources of the elements Co and Mo and if desired K. The aqueous solution A* and the aqueous solution B* are subsequently mixed with one another (preferably, the aqueous solution A* is stirred into the aqueous solution B*). Aqueous silica sol can then, if required, be added as Si source to the resulting aqueous mixture of aqueous solution A* and aqueous solution B*. As regards the pH of the various aqueous solutions, possible sources of the elemental constituents and in respect of the ratio V in the resulting aqueous mixture of aqueous solution A* and aqueous solution B*, what has been said above in connection with the aqueous solutions A, B and the mixture thereof applies analogously.

While the production of the aqueous solutions A, B and the mixture thereof is, as mentioned above, preferably carried out in the presence of gaseous molecular oxygen (e.g. in the presence of air) it has been found to be advantageous in the case of the production of the aqueous solutions A*, B* and the mixture thereof to work in the absence of molecular oxygen.

In general, the aqueous mixture M which can be obtained as described is an aqueous suspension (the ratios V (total molar amount of $NH_3+NH_4^+$ comprised to molar amount of Mo comprised) described as advantageous are preferably likewise present in the aqueous mixture M; in addition, the pH of the aqueous mixture M which can be obtained as described is advantageously ≤3, generally from 0 to 2). According to the invention, aqueous mixtures M which can be obtained as described advantageously comprise not more than or less than 60% of the total amount of Co present therein in dissolved form in the aqueous medium (at the temperature and the working pressure at which the aqueous mixture M was produced. The abovementioned proportion AT of the total amount of Co comprised in the aqueous mixture M which is present in solution in the aqueous medium of the aqueous mixture M is preferably ≤50% and particularly preferably ≤40%, or ≤30% or ≤20%. The total content of Mo, Co, Fe, Bi and Si in the aqueous mixture M to be dried (preferably to be spray dried) is, according to the invention, advantageously from 5 to 25% by weight, advantageously from 8 to 20% by weight, based on the amount of water comprised in the aqueous mixture M. The conversion of the aqueous mixture M into a finely divided intimate dry mix is, according to the invention, preferably carried out by spray drying of the aqueous mixture M. This means that the aqueous mixture M is firstly broken up into fine droplets and these are then dried. According to the invention, spray drying is preferably carried out in a stream of hot air. However, other hot gases can in principle also be used for the abovementioned spray drying (e.g. nitrogen or air diluted with nitrogen or else other inert gases).

In the spray drying step, the droplets can be conveyed either in cocurrent or in countercurrent to the hot gas. Typical gas inlet temperatures are in the range from 250 to 450° C., preferably from 270 to 370° C. Typical gas outlet temperatures are in the range from 100 to 160° C. Spray drying is preferably carried out with the droplets being conveyed in countercurrent to the hot gas.

Of course, the aqueous mixture M can also be dried by means of conventional evaporation (preferably under reduced pressure; the drying temperature will generally not exceed 150° C.). Drying of an aqueous mixture M can in principle also be carried out by freeze drying.

The dried aqueous mixture M can in principle be calcined as such to give a multimetal oxide (active) composition according to the invention of the general stoichiometry I. However, particularly when drying of the aqueous mixture M has been carried out by spray drying, the resulting spray-dried powder is frequently too fine for direct calcination. In this case, the spray-dried powder can be coarsened, for example by subsequent compaction. If compaction is carried out dry, finely divided graphite and/or other shaping aids mentioned in this text (e.g. lubricants and/or reinforcing materials) can, for example, be mixed into the spray-dried powder (e.g, by means of a tumble mixer). For example, compaction can be carried out using a calender having two contrarotating steel rollers. The compacted material can subsequently be comminuted in a targeted manner to the particle size appropriate for further use. This can in the simplest case be carried out by, for example, the compacted material being pressed through a sieve having a defined mesh opening.

However, compaction can in principle also be carried out in a moist state. For example, the spray-dried powder can be kneaded with addition of water. After kneading, the kneaded composition can again be comminuted to the desired fineness appropriate to subsequent use (cf., for example, DE-A 10049873) and dried.

The finely divided precursor materials which can be obtained as described can then be calcined as such and the multimetal oxide (active) composition I powders which can be obtained in this way can be used as such for catalyzing heterogeneously catalyzed partial gas-phase oxidations of, for example, propene to acrolein. As an alternative, the multimetal oxide (active) composition I powder obtained can firstly be shaped to form shaped bodies having a regular or irregular geometry and the resulting shaped bodies can be used as catalysts for the heterogeneously catalyzed partial gas-phase oxidation of, for example, propene to acrolein (cf., for example, DE-A 10063162).

For example, all-active catalysts can be produced from the powder form of the active composition by compaction to give the desired catalyst geometry (e.g. by tabletting, extrusion or ram extrusion), with auxiliaries such as graphite or stearic acid as lubricants and/or mold release agents and reinforcing materials such as microfibers composed of glass, asbestos, silicon carbide or potassium titanate optionally being able to be added. Suitable all-active catalyst geometries are, for example, solid cylinders or hollow cylinders having an external diameter and a length of from 2 to 10 mm. Of course, the all-active catalyst can also have a spherical geometry, with the sphere diameter being able to be from 2 to 10 mm.

Of course, the shaping of the pulverulent active composition can also be effected by application to the outer surface of prefabricated inert catalyst supports. Coating of the shaped support bodies for producing such coated catalysts can, for example, be carried out in a suitable rotatable container, as is known from DE-A 10063162, DE-A 2909671, EP-A 293859, EP-A 714700 and DE-A 4442346.

As an alternative, coating of the shaped support bodies to produce shaped coated catalyst bodies can be carried out using the uncalcined precursor powder and the calcination can be carried out only after application is complete and drying has optionally been carried out (cf., for example, DE-A 10049873).

The shaped support bodies to be used for producing coated catalysts are preferably chemically inert, i.e. they essentially do not intervene in the course of the gas-phase oxidation of, for example, propene to acrolein to be catalyzed. Possible materials for the shaped support bodies are, according to the invention, in particular aluminum oxide, silicon dioxide, silicates such as clay, kaolin, steatite, pumice, aluminum silicate and magnesium silicate, silicon carbide, zirconium dioxide and thorium dioxide (in particular steatite C220 from CeramTec).

The surface of the shaped support body can be either smooth or rough. The surface of the shaped support body is advantageously rough since an increased surface roughness generally results in increased adhesion of the applied coating of finely divided oxidic active composition or finely divided precursor composition. The surface roughness $R_z$ of the shaped support body is frequently in the range from 40 to 200 μm, often in the range from 40 to 100 μm (determined in accordance with DIN 4768 part 1 using a "Hommel Tester für DIN-ISO Oberflächenmaßgrößen" from Hommelwerke, Del.). Furthermore, the support material can be porous or nonporous. The support material is advantageously nonporous (the total volume of the pores based on the volume of the shaped support body is advantageously ≤1% by volume).

The fineness of the finely divided composition to be applied to the surface of the shaped support body is naturally matched to the desired coating thickness. For the range of a coating thickness of from 100 to 500 μm, finely divided compositions of which at least 50% of the powder particles pass a sieve having a mesh opening of from 1 to 10 μm and in which the proportion of particles having a maximum dimension (=longest direct line joining two points present on the surface) above 50 μm is less than 1% (based on the total number of particles), for example, are suitable. In general, the distribution of the maximum dimensions of the powder particles corresponds to a Gauss distribution as a result of the method of production.

To coat the shaped support bodies, the surface of these and/or the finely divided powder composition to be applied is advantageously moistened with a liquid binder (e.g. water or organic solvents such as glycerol or a mixture thereof) and the coated shaped body after application is dried again, e.g. by means of hot air. The layer thickness of the finely divided powder composition applied to the shaped support body is advantageously selected in the range from 10 to 1000 μm, preferably in the range from 100 to 700 μm and particularly preferably in the range from 300 to 500 μm. Possible coating thicknesses are also from 10 to 500 μm or from 200 to 300 μm.

The shaped support body itself can, as mentioned above, have a regular or irregular shape, with preference being given to regularly shaped support bodies such as spheres, solid cylinders or hollow cylinders. For example, the use of spherical shaped support bodies having a diameter of from 1 to 8 mm, preferably from 4 to 5 mm, is suitable according to the invention. However, the use of cylinders having a length of from 2 to 10 mm and an external diameter of from 4 to 10 mm as shaped support bodies is also suitable. In the case of rings which are suitable according to the invention as shaped support bodies, the wall thickness is also usually from 1 to 4 mm. Cylinder dimensions which are suitable for the purposes of the invention are also from 3 to 6 mm (length), from 4 to 8 mm (external diameter) and, in the case of rings, from 1 to 2 mm (wall thickness). Of course, from 2 to 4 mm (length), from 4 to 8 mm (external diameter) and from 1 to 2 mm (wall thickness) is also possible as ring geometry suitable for the purposes of the invention. Support ring geometries which are notable according to the invention are, for example, 7 mm×3 mm×1.5 mm (external diameter×length×wall thickness) and 5 mm×3 mm×1.5 mm (external diameter×length×wall thickness). Specifically, drying and/or thermal treatment (calcination) can be carried out after application of the coating, as described in DE-A 10063162 and DE-A 10049873.

However, it can also be particularly advantageous according to the invention for shaped bodies having a regular or irregular geometry to be produced from a finely divided precursor composition (composed of the finely divided intimate dry mix of the sources of the elemental constituents), advantageously by densification (compression or compaction) and for these then to be converted into all-active shaped catalyst bodies by thermal treatment (calcination).

This procedure is particularly preferred when the intimate mixing of the starting compounds (sources) of the relevant elemental constituents of the multimetal oxide composition I to form the finely divided intimate dry mix is carried out dry (cf., for example, WO 2008/087116 and DE-A 102008042060).

As further finely divided shaping aids, it is once again possible to add, for example, lubricants such as graphite, carbon black, polyethylene glycol, polyacrylic acid, stearic acid, starch, mineral oil, vegetable oil, water, boron trifluoride and/or boron nitride. Further possible shaping aids are reinforcing materials such as microfibers composed of glass, asbestos, silicon carbide or potassium titanate which, after completion of shaping by compaction, have a positive effect on the cohesion of the compact obtained (the resulting shaped body). Concomitant use of lubricants in such a shaping step is described, for example, in the documents DE-A 102007004961, WO 2008/087116, WO 2005/030393, US-A 2005/0131253, WO 2007/017431, DE-A 102007005606 and DE-A 102008040093.

According to the invention, preference is given to using exclusively finely divided graphite as lubricant. Possible finely divided graphites to be used are, in particular, those recommended in the documents WO 2005/030393, US-A 2005/0131253, WO 2008/087116 and DE-A 102007005606. This applies particularly to those graphites which are used in the examples and comparative examples in these documents. Very particularly preferred graphites are Asbury 3160 and Asbury 4012 from Asbury Graphite Mills, Inc., New Jersey 08802, USA, and Timrex®T44 from Timcal Ltd., 6743 Bodio, Switzerland.

Based on the weight of the finely divided precursor composition to be shaped, this composition can comprise, for example, up to 15% by weight of finely divided lubricant (e.g. graphite). However, the lubricant content of the finely divided precursor composition to be shaped (in the finely divided intimate dry mix) is usually ≤9% by weight, frequently ≤5% by weight, often ≤4% by weight, particularly when the finely divided lubricant is graphite. In general, the abovementioned amount added is ≥0.5% by weight, usually ≥2.5% by weight.

In general, the compaction of the finely divided precursor composition optionally comprising shaping aids (the finely divided intimate dry mix) to give the desired geometry of the shaped body (the geometric shaped catalyst precursor body) is effected by action of external forces (pressure) on the precursor composition. The shaping apparatus to be employed or the shaping method to be employed is not subject to any restriction.

For example, the compacting shaping can be carried out by means of ram extrusion, tabletting or screw extrusion. Here, the finely divided precursor composition (the finely divided intimate dry mix) is preferably dry to the touch when used. However, it can also comprise, for example, up to 10 times its total weight of added substances which are liquid under standard conditions (25° C., 1 atm (1.01 bar)). The finely divided precursor composition (the finely divided intimate dry mix) can also comprise solid solvates (e.g. hydrates) which comprise such liquid substances in chemically and/or physically bound form. Of course, the finely divided precursor composition can also be completely free of such substances.

A shaping process which is preferred according to the invention for compacting the finely divided precursor composition (the finely divided intimate dry mix) is tabletting. The fundamentals of tabletting are described, for example, in "Die Tablette", Handbuch der Entwicklung, Herstellung and Qualitätssicherung, W. A. Ritschel and A. Bauer-Brandl, 2nd edition, Edition Verlag Aulendorf, 2002, and can be applied in a completely analogous manner to the tabletting process required here.

Tabletting for the purposes of the invention is advantageously carried out as described in the documents WO 2005/030393, DE-A 102008040093, DE-A 102008040094 and WO 2007/017431. The temperature around the tabletting machine is normally 25° C. The particle diameters of the precursor composition (the finely divided intimate dry mix) to be compacted are, for practical purposes, advantageously, if desired as a result of precoarsening by compaction, in the range from 100 to 2000 µm, preferably from 150 to 1500 µm, particularly preferably from 400 to 1250 µm, or from 400 to 1000 µm, or from 400 to 800 µm (shaping aid mixed in before compaction is not taken into account).

Like the shaping apparatus to be used for compaction or the shaping method to be used, the desired geometry of the resulting shaped bodies is not subject to any restriction in the process of the invention, i.e. the shaped catalyst precursor bodies produced by compaction can have either a regular or irregular shape, with regularly shaped bodies generally being preferred for the purposes of the invention.

For example, the shaped catalyst precursor body can have a spherical geometry. The sphere diameter here can be, for example, from 2 to 10 mm, or from 4 to 8 mm. However, the geometry of the shaped catalyst precursor body can also be that of a solid cylinder or a hollow cylinder (ring-shaped). In both cases, external diameter and height (length) can be, for example, from 2 to 10 mm, or from 2 to 8 mm, or from 3 to 8 mm.

In the case of hollow cylinders (rings), a wall thickness of from 1 to 3 mm is generally advantageous. Of course, all those geometries which are disclosed and recommended in WO 02/062737 are possible as catalyst precursor geometries. In the case of solid cylinders, the external diameter can also be from 1 to 10 mm.

The shaping pressures employed in a compaction of finely divided precursor composition (finely divided intimate dry mix) to be carried out as described will, according to the invention, advantageously be from 50 kg/cm$^2$ to 5000 kg/cm$^2$. The shaping pressures are preferably from 200 to 3500 kg/cm$^2$, particularly preferably from 600 to 2500 kg/cm$^2$.

Especially in the case of ring-shaped precursor bodies, (which are also referred to, regardless of their shape, as green bodies in the literature), the shaping compaction according to the invention should, according to the invention, advantageously be carried out so that the lateral compressive strength LCS of the resulting shaped body (cf. DE-A 102008040093, DE-A 102008040094 and WO 2005/030393) fulfils the relationship 12 N≤LCS≤35 N, preferably 15 N≤LCS≤30 N, and particularly preferably 19 N≤LCS≤30 N.

The experimental determination of the lateral compressive strength is carried out as described in the documents WO 2005/030393 and WO 2007/017431. Of course, ring-like green bodies as recommended by DE-A 102008040093 are very particularly preferred according to the invention. The end face of ring-shaped or ring-like shaped bodies can in the case of green bodies according to the invention in the production process described be either curved or not curved (cf., in particular, DE-A 102007004961, EP-A 184790 and DE-A 102008040093). Such curvature is not taken into account in determining the height of such geometric shaped bodies.

Ring geometries which are particularly advantageous according to the invention of shaped bodies which can be obtained by compaction of finely divided precursor composition (finely divided intimate dry mix) fulfil the condition Height/External diameter=H/E=0.3 to 0.7. H/E is particularly preferably from 0.4 to 0.6. Furthermore, it is advantageous in the case of ring-shaped or ring-like green bodies according to the invention for the ratio I/E (where I is the Internal diameter of the ring geometry) to be from 0.3 to 0.7, preferably from 0.4 to 0.7.

Abovementioned ring geometries which simultaneously have one of the advantageous H/E ratios and one of the advantageous I/E ratios are particularly advantageous. Such possible combinations are, for example, H/E=0.3 to 0.7 and I/E=0.3 to 0.8 or 0.4 to 0.7. As an alternative, H/E can be from 0.4 to 0.6 and I/E can at the same time be from 0.3 to 0.8 or from 0.4 to 0.7. Furthermore, it is advantageous in the case of the relevant ring geometries for H to be from 2 to 6 mm and preferably from 2 to 4 mm. Furthermore, it is advantageous for E in the case of the rings to be from 4 to 8 mm, preferably from 4 to 6 mm. The wall thickness of green body ring geometries which are preferred according to the invention is from 1 to 1.5 mm.

Possible ring geometries according to the invention are thus (E×H×I) 5 mm×2 mm×2 mm, or 5 mm×3 mm×2 mm, or 5 mm×3 mm×3 mm, or 5.5 mm×3 mm×3.5 mm, or 6 mm×3 mm×4 mm, or 6.5 mm×3 mm×4.5 mm, or 7 mm×3 mm×5 mm, or 7 mm×7 mm×3 mm, 7 mm×3 mm×4 mm, or 7 mm×7 mm×4 mm.

In general, it is found to be advantageous for the process of the invention when each of the sources used for producing the finely divided intimate dry mixes to be produced from the sources of the elemental constituents other than oxygen of the multimetal oxide composition I goes through a dispersion step during the course of the production of the finely divided intimate dry mix to produce a diameter of the dry mix $d^S_{90}$ of ≤5 µm.

The requirement $d^S_{90} \leq 5$ μm is fulfilled basically when a Source is dissolved in a solvent (the term "dissolve" is here meant in the sense of a molecular or ionic solution). This results from the source being molecularly or ionically dispersed in the solvent on dissolution of a source (starting compound) in a solvent. This means that the largest geometric unit of the dissolved starting substance (source) present in the solution must have "molecular" dimensions which are thus necessarily essentially smaller than 5 μm (as stated above, a starting compound can be source of more than one element and a solution can have more than one source present in dissolved form).

The requirement $d^S_{90} \leq 5$ μm is also fulfilled when a Source of an element is present in colloidal solution in a solvent, since the units present therein in solution have a diameter of only from 1 to 250 nm, so that the associated $d^S_{90}$ is necessarily $\leq 5$ μm.

However, the requirement $d^S_{90} \leq 5$ μm is also fulfilled when a source is, for example, comminuted dry to this particle size (e.g. by milling).

Here, the particle diameter $d^S_{90}$ relates to the particle diameter distribution of the dry powder, which is to be determined as follows.

The finely divided powder is introduced via a dispersing chute into the dry disperser Scirocco 2000 (from Malvern Instruments Ltd., Worcestershire WR14 1AT, United Kingdom), there dispersed dry by means of compressed air and blown as a free jet into the measurement cell. In the latter, the volume-based particle diameter distribution is then determined in accordance with ISO 13320 by means of the Malvern Mastersizer S laser light scattering spectrometer (likewise from Malvern Instruments Ltd.).

A particle diameter $d_x$ based on such a particle diameter distribution is defined so that X % of the total particle volume is made up of particles having this diameter or a smaller diameter. That is to say, (100–X) % of the total particle volume is made up of particles having a diameter of $>d_x$. Unless explicitly indicated otherwise in this text, particle diameter determinations and $d_x$ values derived therefrom, e.g. $d_{90}$, $d_{50}$ and $d_{10}$, are based on a dispersing pressure employed in the determination (which determines the degree of dispersion of the dry powder during the measurement) of 2 bar absolute. $D^S_{90}$ is such a particle diameter $d_{90}$ of a pulverulent Source.

All information given in this text in respect of an X-ray diffraction pattern are based on an X-ray diffraction pattern produced using Cu—$K_\alpha$ radiation as X-radiation (Theta-Theta Bruker D8 Advance diffractometer, tube voltage: 40 kV, tube current: 40 mA, aperture V20 (variable), antiscatter orifice V20 (variable), detector orifice (0.1 mm), measurement interval (2Θ=2 theta): 0.02°, measurement time per step: 2.4 s, detector: Si semiconductor detector).

All information in this text in respect of specific surface areas of solids are based on determinations in accordance with DIN 66131 (determination of the specific surface area of solids by gas adsorption ($N_2$) using the Brunauer-Emmert-Teller (BET) method), unless explicitly indicated otherwise.

All information in this text in respect of total pore volumes and also in respect of pore diameter distributions of these total pore volumes are based on determinations using the method of mercury porosimetry and the instrument Auto Pore 9500 from Micromeritics GmbH, D-41238 Mönchengladbach (band width 0.003-300 μm).

According to the invention, all-active shaped catalyst precursor bodies advantageously have a very low residual moisture content. This applies particularly when the intimate mixing of the various sources of the elemental constituents other than oxygen of the multimetal oxide composition I has been carried out wet (particularly when it has been carried out with formation of an aqueous mixture M).

According to the invention, the residual moisture content of green bodies which are advantageous according to the invention is preferably $\leq 10\%$ by weight, better $\leq 8\%$ by weight, even better $\leq 6\%$ by weight and best $\leq 4\%$ by weight or $\leq 2\%$ by weight (the residual moisture determination can be carried out as described in "Die Bibliothek der Technik", Volume 229, "Thermogravimetrische Materialfeuchtebestimmung", Fundamentals and practical applications, Horst Nagel, verlag moderne industrie (e.g. using a Computrac MAX 5000 XL from Arizona Instruments)).

If the green bodies are derived from an aqueous mixture M (so that their moisture content comprises water), the residual moisture determination is advantageously carried out using microwaves (e.g. using the microwave system LB 456 from BERTHOLD TECHNOLOGIES).

In this procedure, the microwave radiates at a very low power (0.1 mW) through the material to be examined (the latter experiences essentially no change in its temperature as a result of the comparatively low power). The material constituents are polarized to differing extents as a result. As a result, the microwave loses speed and energy. Here, the influence of water molecules is substantially greater than the influence of other constituents, which makes the selective redetermination of residual water contents possible. This is due to water molecules being able, owing to their size and their dipole property, to follow an alternating electromagnetic field in the microwave frequency range particularly well by dipole alignment. In the process, they absorb energy and their electrical properties change the alternating electromagnetic field. The measurement principle is based on this weakening of the field and change in the field. For example, a weak microwave field can be built up over the sensor surface of a planar sensor and the resonance frequency of the sensor system can be continually analyzed by scanning the microwave frequency. If a water-comprising material to be measured is then brought over the sensor, the resonance frequency shifts and its amplitude is damped. Both damping and resonance frequency shift increase with increasing amount of water, i.e. with increasing bulk density of the material being measured. However, the ratio of frequency shift and damping is a density-independent measure of the percentage of water and thus the key to the moisture measurement. The ratio thus forms the microwave moisture measurement value which represents the total moisture content. Since the microwave resonance method is an indirect moisture measurement method, calibration is necessary. In such a calibration measurement, material samples having a defined moisture content are measured by means of the sensor. The relationship between the measured microwave moisture values and the associated defined absolute moisture contents of the material then form the calibration of the measurement system. The measurement accuracy is usually ±0.1% of moisture (for example, the water moisture content can be determined by means of an online moisture measurement instrument PMD300PA from Sartorius).

In the light of this background, spray drying of a wet (e.g. aqueous) mixture M can be carried out in such a way that the resulting spray-dried powder has a very low residual moisture content.

Green bodies produced according to the invention should, taking into account the aspect just addressed, ideally be stored with exclusion of (moisture-comprising) ambient air (storage until calcination is preferably carried out under water-free inert gas or under previously dried air).

According to the invention, the shaping of the finely divided intimate dry mix is carried out with exclusion of (moisture-comprising) ambient air (e.g. under an $N_2$ atmosphere).

The calcination of the green bodies (or generally of finely divided precursor powder or of shaped support bodies coated with this) is normally carried out at temperatures which reach at least 350° C. or generally exceed this value. However, a temperature of 650° C. is normally not exceeded in the calcination (the term calcination temperature in this text means the temperature present in the material being calcined). According to the invention, a temperature of 600° C., preferably a temperature of 550° C. and frequently a temperature of 500° C., is advantageously not exceeded during the calcination. Furthermore, a temperature of 380° C., advantageously a temperature of 400° C., particularly advantageously a temperature of 420° C. and very particularly preferably a temperature of 440° C., is preferably exceeded in the above calcination. The calcination can also be divided into a plurality of sections over time.

On the basis of experience, the calcination is preferably preceded by a thermal treatment at temperatures of from ≥120° C. to <350° C., preferably from ≥150° C. to ≤320° C., particularly preferably from ≥220° C. to ≤290° C.

Such a thermal treatment is advantageously carried out until the constituents which are comprised in the composition to be treated thermally and decompose into gaseous compounds under the conditions of the thermal treatment have been largely (preferably completely) decomposed into gaseous compounds (the time required for this can be, for example, from 3 h to 10 h, frequently from 4 h to 8 h). This is generally the case when, firstly, the molar amount of cations other than metal ions comprised in the composition subsequently to be calcined is, based on the total molar amount of cations comprised, ≤20 mol % (preferably ≤10 mol %) and, secondly, the molar amount of anions other than $O^{2-}$ comprised in the same composition is, based on the total molar amount of anions comprised, likewise ≤20 mol % (preferably ≤10 mol %).

Temperature windows which are, according to the invention, advantageous for the final calcination temperature are therefore in the temperature range from 400° C. to 600° C. or preferably in the temperature range from 420 to 550° C. or particularly preferably in the temperature range from 400 to 500° C.

The total calcination time is generally more than 10 hours. Treatment times of 45 hours or 25 hours are usually not exceeded in the calcination. The total calcination time is often below 20 hours. Basically, a shorter calcination time is generally sufficient at higher calcination temperatures than at lower calcination temperatures.

In an embodiment of the calcination which is advantageous according to the invention, a temperature of 500° C. is not exceeded and the calcination time in the temperature window from ≥430° C. to ≤500° C. is from >10 to ≤20 h.

The entire thermal treatment (including a decomposition phase) of a precursor composition (e.g. a green body) can be carried out either under inert gas or under an oxidizing atmosphere such as air (or another mixture of inert gas and molecular oxygen) or under a reducing atmosphere (e.g. a mixture of inert gas, $NH_3$, CO and/or $H_2$ or under methane, acrolein, methacrolein). It goes without saying that the thermal treatment can also be carried out under reduced pressure. The atmosphere can also be varied over the course of the thermal treatment.

According to the invention, the thermal treatment (in particular the calcination phase) is preferably carried out in an oxidizing atmosphere. This advantageously consists predominantly of stationary or (preferably) moving air, (particular preference is given to a stream of air being passed through the composition to be treated thermally (the material to be calcined)). However, the oxidizing atmosphere can likewise comprise a stationary or moving mixture of, for example, 25% by volume of $N_2$ and 75% by volume of air, or 50% by volume of $N_2$ and 50% by volume of air, or 75% by volume of $N_2$ and 25% by volume of air (a treatment atmosphere composed of 100% by volume of $N_2$ is likewise possible).

In principle, the thermal treatment (e.g. the calcination) of the precursor composition (e.g. the green bodies) can be carried out in various types of furnace, e.g. heatable convection chambers (convection furnaces, e.g. convection shaft furnaces), tray furnaces, rotary tube furnaces, belt calciners or shaft furnaces. According to the invention, the thermal treatment (e.g. the calcination) is advantageously carried out in a belt calciner as recommended in DE-A 10046957 and WO 02/24620. Hot spot formation within the material to be treated (within the material to be calcined) is largely avoided by increased volume flows of calcination atmosphere through the material being calcined being assisted by a gas-permeable conveyor belt carrying the material being calcined and the use of fans.

In the thermal treatment of the precursor compositions (e.g. the green bodies) to be carried out as described, concomitantly used shaping aids can be retained both in the resulting shaped catalyst body and also be at least partly given off therefrom in gaseous form due to thermal and/or chemical decomposition into gaseous compounds (e.g. CO, $CO_2$). Shaping aids remaining in the shaped catalyst body act, in a catalytic use of the catalyst body, essentially exclusively as diluents for the multimetal oxide I active composition. In principle, the thermal treatment can in this respect be carried out as described in US 2005/0131253.

The lateral compressive strengths of ring-shaped all-active shaped catalyst bodies which can be obtained as described are typically from 5 to 15 N, frequently from 6 to 13 N or from 8 to 11 N.

The specific (BET) surface area of multimetal oxide (active) compositions I according to the invention (particularly when they are, as described above, shaped to form ring-shaped all-active catalysts) is advantageously from 2 to 20 or up to 15 $m^2/g$, preferably from 3 to 10 $m^2/g$ and particularly preferably from 4 to 8 $m^2/g$. The associated total pore volume is, according to the invention, advantageously in the range from 0.1 to 1 $cm^3/g$ or up to 0.8 $cm^3/g$, preferably in the range from 0.1 to 0.5 $cm^3/g$ and particularly preferably in the range from 0.2 to 0.4 $cm^3/g$.

If the pore diameter in μm is plotted on the abscissa and the logarithm of the differential contribution in $cm^3/g$ of the respective pore diameter to the total pore volume in $cm^3/g$ is plotted on the ordinate, multimetal oxide (active) compositions I which are particularly useful according to the invention (in particular when, as described above, they have been shaped to form ring-shaped all-active catalysts) generally display a monomodal distribution (having only one maximum). If the contribution of pores having a pore radius of ≤0.1 μm to the total pore volume is ≤0.05 $cm^3/g$, particularly good total target product selectivities (e.g. in the case of a heterogeneously catalyzed partial oxidation of propene to acrolein and/or acrylic acid) result. If the contribution of such comparatively narrow pores to the total pore volume is >0.05 $cm^3/g$, a reduction in this contribution, which is advantageous according to the invention, can be brought about by increasing the calcination time and/or the calcination temperature.

Furthermore, it is also found to be advantageous for an increased total target product selectivity for the contribution of pores having a pore radius in the range from 0.2 to 0.4 μm to the total pore volume, based on the total pore volume, to be ≥70% by volume, advantageously ≥75% by volume, particularly advantageously ≥85% by volume, preferably ≥90% by volume, particularly preferably ≥95% by volume.

Of course, the multimetal oxide (active) composition according to the invention of the general stoichiometry I can also be used diluted with inert materials for the catalysis of heterogeneously catalyzed partial gas-phase oxidations. Suitable inert diluent materials of this type are, inter alia, element oxides such as aluminum oxide, silicon oxide, thorium dioxide and zirconium dioxide which have been calcined at high temperatures and therefore have a comparatively low porosity. However, finely divided silicon carbide or finely divided silicates such as magnesium silicate and aluminum silicate or steatite can also be used for the abovementioned purpose. The calcined multimetal oxide (active) composition of the general stoichiometry I is, for example, advantageously milled to a fine powder. This is then advantageously mixed with finely divided diluent material and the resulting mixed powder is shaped to form a geometric shaped body using one of the shaping processes described in this text (preferably by tabletting). This is then converted into the corresponding shaped catalyst body by being calcined again. It goes without saying that the finely divided inert diluent material can also, for example, be incorporated into a wet (e.g. aqueous) mixture M before drying of the latter. Furthermore, finely divided inert diluent material can be incorporated into a finely divided dry mix of sources of the elemental constituents of the multimetal oxide composition I. However, such procedures are less preferred according to the invention.

Multimetal oxide (active) compositions of the general stoichiometry I produced by the advantageous production methods described (or all-active shaped catalyst bodies comprising these compositions), in particular, display essentially no local sites composed of element oxides (e.g. iron oxide or cobalt oxide). Rather, these elements are largely constituents of complex, mixed, Fe-, Co- and Mo-comprising oxomolybdates. This has been found to be advantageous in respect of a minimization, which is sought according to the invention, of unwanted total combustion of organic reaction gas mixture constituents in the relevant heterogeneously catalyzed partial oxidations.

Multimetal oxide (active) compositions according to the invention of the general stoichiometry I are suitable as active compositions for the catalysis of heterogeneously catalyzed partial gas-phase oxidations of alkanes, alkanols, alkenes and/or alkenals having from 3 to 6 carbon atoms (for the purposes of the present text, partial oxidations are, in particular, reactions of organic compounds involving reaction of molecular oxygen in which the organic compound to be partially oxidized comprises at least one more chemically bound oxygen atom after the reaction is complete than before the partial oxidation is carried out). However, for the purposes of the present text, the term partial oxidation also comprises oxidative dehydrogenation and partial ammoxidation, i.e. a partial oxidation in the presence of ammonia.

Multimetal oxide (active) compositions according to the invention of the general stoichiometry I are particularly suitable for the catalysis of the heterogeneously catalyzed partial gas-phase oxidation of propene to acrolein, of isobutene to methacrolein and also for the catalysis of the heterogeneously catalyzed partial gas-phase ammoxidation of propene to acrylonitrile and also of isobutene to methacrylonitrile.

As mentioned above, the heterogeneously catalyzed partial gas-phase oxidation of propene (isobutene and/or tert-butanol) to acrolein (methacrolein) forms the first stage of a two-stage heterogeneously catalyzed partial gas-phase oxidation of propene (isobutene and/or tert-butanol) to acrylic acid (methacrylic acid), as described by way of example in WO 2006/42459.

A formation of acrylic acid (methacrylic acid) as by-product in a heterogeneously catalyzed partial gas-phase oxidation of propene (isobutene) to acrolein (methacrolein) is therefore generally not undesirable and is normally subsumed under the desired formation of the product of value.

What has been said above applies particularly to ring-shaped all-active shaped catalyst bodies according to the invention comprising multimetal oxide compositions of the general stoichiometry I.

The heterogeneously catalyzed partial oxidation (in particular that of propene to acrolein) can, for example, be carried out as described in the documents DE-A 102007004961, WO 02/49757, WO 02/24620, DE-A 102008040093, WO 2005/030393, EP-A 575897, WO 2007/082827, WO 2005/113127, WO 2005/047224, WO 2005/042459, WO 2007/017431, DE-A 102008042060, WO 2008/087116, DE-A 102010048405, DE-A 102009047291, DE-A 102008042064, DE-A 102008042061 and DE-A 102008040094.

Here, the ring geometries emphasized individually in the present text of the ring-shaped all-active catalysts which can be obtained as described are found to be particularly advantageous even when the space velocity of the reaction gas starting mixture comprising propene, isobutene and/or tert-butanol (or the methyl ether thereof) over the catalyst charge is ≥130 standard l/l of catalyst charge·h (beds of pure inert material upstream and/or downstream of the active catalyst are not considered to be part of the catalyst charge for the calculation of the space velocity in this text; the volume of the catalyst charge is the bed volume of the catalyst present in the reactor).

The advantage of ring-shaped all-active shaped catalyst bodies which can be obtained as described (or other catalysts (shaped catalyst bodies) comprising multimetal oxide (active) compositions of the general stoichiometry I) is however also present when the abovementioned space velocity over the catalyst charge is ≥140 standard l/l·h, or ≥150 standard l/l·h, or ≥160 standard l/l·h. Normally, the abovementioned space velocity over the catalyst charge will be ≤600 standard l/l·h, frequently ≤500 standard l/l·h, often ≤400 standard l/l·h or ≤350 standard l/l·h. Space velocities in the range from ≥160 standard l/l·h to ≤300 or ≤250 or ≤200 standard l/l·h are particularly advantageous.

For the purposes of the present text, the space velocity of a reaction gas starting mixture over a fixed catalyst bed is the amount of reaction gas starting mixture in standard liters (=standard l; the volume in liters which the corresponding amount of reaction gas starting mixture would occupy at STP, i.e. at 0° C. and 1 atm (1.01 bar)) fed to the fixed catalyst bed divided by the volume of this bed (bed sections composed of pure inert material are not included), i.e. its bed volume, per hour (→unit=standard l/l·h).

The space velocity can also be based on only one constituent of the reaction gas starting mixture (i.e. only on the organic starting compound to be partially oxidized). It is then the volume of this constituent (e.g. the organic starting compound of the partial oxidation) which is fed to the fixed catalyst bed divided by the volume of this bed, per hour.

Of course, catalysts which can be obtained according to the invention (e.g. ring-shaped all-active shaped catalyst bodies) can also be operated in an inventively advantageous manner as catalysts for the partial oxidation of propene to acrolein or of isobutene and/or tert-butanol (or the methyl ether thereof) to methacrolein at space velocities of the starting compound to be partially oxidized over the catalyst charge of ≤130 standard l/l·h, or ≤120 standard l/l·h, or ≤110 standard l/l·h. However, this space velocity will generally be ≥60 standard l/l·h, or ≥70 standard l/l·h, or ≥80 standard l/l·h.

In principle, the space velocity of the starting compound to be partially oxidized (propene, isobutene and/or tert-butanol (or the methyl ether thereof)) over the catalyst charge can be set by means of two setting parameters:

a) the space velocity of the reaction gas starting mixture (the reaction gas mixture fed to the fixed catalyst bed) over the catalyst charge and/or
b) the content of the starting compound to be partially oxidized in the reaction gas starting mixture.

The catalysts (e.g. ring-shaped all-active shaped catalyst bodies) which can be obtained according to the invention are also particularly suitable when, at space velocities of the organic compound to be partially oxidized over the catalyst charge above 130 standard l/l·h, the setting of the space velocity is carried out primarily by means of the abovementioned setting parameter a).

The propene content (isobutene content or tert-butanol content (or the methyl ether content)) of the reaction gas starting mixture is usually (i.e. essentially independently of the space velocity) from 4 to 20% by volume, frequently from 5 to 15% by volume or from 5 to 12% by volume, or from 5 to 8% by volume (in each case based on the total volume (flow) of the reaction gas starting mixture).

The gas-phase partial oxidation process of the partial oxidation catalyzed by the catalysts which can be obtained as described (e.g. ring-shaped all-active shaped catalyst bodies or other geometric shaped catalyst bodies) will frequently be carried out (essentially independently of the space velocity) at a volume ratio of (organic) compound to be partially oxidized (e.g. propene:oxygen:indifferent gases (including water vapor) in the reaction gas starting mixture of 1:(1.0-3.0):(5-25), preferably 1:(1.5-2.3):(10-20).

Indifferent gases (or inert gases) are gases which remain chemically unchanged to an extent of at least 95 mol %, preferably at least 98 mol %, during the partial oxidation.

In the reaction gas starting mixtures described above, the indifferent gas can comprise ≥20% by volume, or ≥30% by volume, or ≥40% by volume, or ≥50% by volume, or ≥60% by volume, or ≥70% by volume, or ≥80% by volume, or ≥90% by volume, or ≥95% by volume, of molecular nitrogen.

However, in the case of space velocities of the organic compound to be partially oxidized over the catalyst charge of ≥150 standard l/l·h, the concomitant use of inert diluent gases such as propane, ethane, methane, pentane, butane, $CO_2$, CO, steam or noble gases is advisable (but not absolutely necessary) for the reaction gas starting mixture. In general, these inert gases and mixtures thereof can also be used at lower space velocities of the organic compound to be partially oxidized over the catalyst charge. Recycle gas can also be concomitantly used as diluent gas. For the present purposes, recycle gas is the residual gas which remains when the target compound is essentially selectively separated off from the product gas mixture from the partial oxidation. It has to be taken into account that the partial oxidations to form acrolein or methacrolein using the, for example, ring-shaped catalyst bodies which can be obtained according to the invention can be only the first stage of a two-stage partial oxidation to form acrylic acid or methacrylic acid as the actual target compounds, so that the recycle gas is then mostly formed only after the first stage. In such a two-stage partial oxidation, the product gas mixture from the first stage is generally fed as such, optionally after cooling and/or addition of secondary oxygen (in general as air), to the second partial oxidation stage.

In the partial oxidation of propene to acrolein using the catalysts which can be obtained as described (e.g. ring-shaped catalyst bodies), a typical composition of the reaction gas starting mixture measured at the inlet of the reactor can (independently of the space velocity selected) comprise, for example, the following components:

from 6 to 6.5% by volume of propene,
from 1 to 3.5% by volume of $H_2O$,
from 0.2 to 0.5% by volume of CO,
from 0.6 to 1.2% by volume of $CO_2$,
from 0.015 to 0.04% by volume of acrolein,
from 10.4 to 11.3% by volume of $O_2$, and
molecular nitrogen as balance to 100% by volume;

or:

5.6% by volume of propene,
10.2% by volume of oxygen,
1.2% by volume of $CO_x$,
81.3% by volume of $N_2$, and
1.4% by volume of $H_2O$.

The first compositions are particularly suitable at space velocities of propene of ≥130 standard l/l·h and the latter composition is particularly suitable at space velocities of propene of <130 standard l/l·h, in particular 100 standard l/l·h, over the fixed catalyst bed.

As alternative compositions of the reaction gas starting mixture, possibilities for a partial oxidation of propene to acrolein are (independently of the space velocity selected) compositions having the following component contents:

from 4 to 25% by volume of propene,
from 6 to 70% by volume of propane,
from 5 to 60% by volume of $H_2O$,
from 8 to 65% by volume of $O_2$, and
from 0.3 to 20% by volume of $H_2$;

or from 4 to 25% by volume of propene,
from 6 to 70% by volume of propane,
from 0 to 60% by volume of $H_2O$,
from 8 to 16% by volume of $O_2$,
from 0 to 20% by volume of $H_2$,
from 0 to 0.5% by volume of CO,
from 0 to 1.2% by volume of $CO_2$,
from 0 to 0.04% by volume of acrolein,
and essentially $N_2$ as balance to 100% by volume;

or from 50 to 80% by volume of propane,
from 0.1 to 20% by volume of propene,
from 0 to 10% by volume of $H_2$,
from 0 to 20% by volume of $N_2$,
from 5 to 15% by volume of $H_2O$, and
the amount of molecular oxygen required for the molar ratio of oxygen content to propene content to be from 1.5 to 2.5, or from 6 to 9% by volume of propene,
from 8 to 18% by volume of molecular oxygen,
from 6 to 30% by volume of propane and
from 32 to 72% by volume of molecular nitrogen.

However, the reaction gas starting mixture for a heterogeneously catalyzed partial oxidation of propene to acrolein using catalysts according to the invention can also have the following composition:
- from 4 to 15% by volume of propene,
- from 1.5 to 30% by volume (frequently from 6 to 15% by volume) of water,
- from ≥0 to 10% by volume (preferably from ≥0 to 5% by volume) of constituents other than propene, water, oxygen and nitrogen, the amount of molecular oxygen required for the molar ratio of molecular oxygen comprised to molecular propene comprised to be from 1.5 to 2.5 and molecular nitrogen as balance to a total amount of 100% by volume.

Another possible reaction gas starting mixture composition can comprise:
- 6.0% by volume of propene,
- 60% by volume of air, and
- 34% by volume of $H_2O$.

As an alternative, reaction gas starting mixtures having the composition as per example 1 of EP-A 990 636, or as per example 2 of EP-A 990 636, or as per example 3 of EP-A 1 106 598, or as per example 26 of EP-A 1 106 598, or as per example 53 of EP-A 1 106 598 can also be used for a partial oxidation of propene to acrolein according to the invention.

The catalysts according to the invention which can be obtained as described, e.g. ring-shaped catalyst bodies, are also suitable for the processes of DE-A 10246119 and DE-A 10245585.

Further reaction gas starting mixtures which are suitable for the purposes of the invention can come within the following composition range:
- from 7 to 11% by volume of propene,
- from 6 to 12% by volume of water,
- from ≥0 to 5% by volume of constituents other than propene, water, oxygen and nitrogen,
- the amount of molecular oxygen required for the molar ratio of molecular oxygen comprised to propene comprised to be from 1.6 to 2.2, and molecular nitrogen as balance to a total amount of 100% by volume.

In the case of methacrolein as target compound, the reaction gas starting mixture can, in particular, also have the composition described in DE-A 44 07 020.

The reaction temperature for a heterogeneously catalyzed partial oxidation of propene to acrolein according to the invention when using the catalysts according to the invention which can be obtained as described (e.g. ring-shaped catalyst bodies) is frequently from 300 to 450° C., or up to 400° C. or up to 380° C. The same applies in the case of methacrolein as target compound.

The reaction pressure in the abovementioned partial oxidations is generally from 0.5 to or from 1.5 to 3 or to 4 bar (in the present text, pressures are always, unless explicitly stated otherwise, absolute pressures).

The total space velocity of reaction gas starting mixture over the catalyst charge is typically from 1000 to 10 000 standard l/l·h, usually from 1500 to 5000 standard l/l·h and often from 2000 to 4000 standard l/l·h, in the abovementioned partial oxidations.

As propene to be used in the reaction gas starting mixture, it is possible to use, in particular, polymer grade propene and chemical grade propene, as described, for example, by DE-A 102 32 748.

Air is normally used as oxygen source.

The partial oxidation using the catalysts according to the invention which can be obtained as described (e.g. the ring-shaped catalyst bodies) can in the simplest case be carried out, for example, in a single-zone multiple catalyst tube fixed-bed reactor as described by DE-A 44 31 957, EP-A 700 714 and EP-A 700 893.

The catalyst tubes in the abovementioned shell-and-tube reactors are usually made of ferritic steel and typically have a wall thickness of from 1 to 3 mm. Their internal diameter is generally from 20 to 30 mm, frequently from 21 to 26 mm. A typical catalyst tube length is, for example, 3.20 m. The number of catalyst tubes accommodated in the shell-and-tube reactor is advantageously at least 1000, preferably at least 5000. The number of catalyst tubes accommodated in the reactor shell is frequently from 15 000 to 35 000. Shell-and-tube reactors having more than 40 000 catalyst tubes tend to be the exception. Within the shell, the catalyst tubes are normally homogeneously distributed, with the distribution advantageously being selected so that the distance between the central internal axes of closest catalyst tubes (known as the catalyst tube spacing) is from 35 to 45 mm (cf. EP-B 468 290).

However, the partial oxidation can also be carried out in a multizone (e.g. "two-zone") multiple catalyst tube fixed-bed reactor as recommended by DE-A 199 10 506, DE-A 103 13 213, DE-A 103 13 208 and EP-A 1 106 598, in particular at relatively high space velocities of the organic compound to be partially oxidized over the catalyst charge. A typical catalyst tube length in the case of a two-zone multiple catalyst fixed-bed reactor is 3.50 m. All else applies essentially as described for the single-zone multiple catalyst tube fixed-bed reactor. A heat transfer medium is passed around the catalyst tubes within which the catalyst charge is located in each temperature zone. Suitable heat transfer media are, for example, melts of salts such as potassium nitrate, potassium nitrite, sodium nitrite and/or sodium nitrate or of low-melting metals such as sodium, mercury and alloys of various metals. The flow rate of the heat transfer medium within the respective temperature zone is generally selected so that the temperature of the heat transfer medium increases by from 0 to 15° C., frequently from 1 to 10° C., or from 2 to 8° C., or from 3 to 6° C., from the point of entry into the temperature zone to the exit from the temperature zone.

The inlet temperature of the heat transfer medium, which, viewed over the respective temperature zone, can be conveyed in cocurrent or in countercurrent to the reaction gas mixture, is preferably selected as recommended in the documents EP-A 1 106 598, DE-A 199 48 523, DE-A 199 48 248, DE-A 103 13 209, EP-A 700 714, DE-A 103 13 208, DE-A 103 13 213, WO 00/53557, WO 00/53558, WO 01/36364, WO 00/53557 and the other documents cited as prior art in the present text. Within the temperature zone, the heat transfer medium is preferably conveyed in a meandering fashion. In general, the multiple catalyst tube fixed-bed reactor additionally has temperature sensor tubes for determining the gas temperature in the catalyst bed. The internal diameter of the temperature sensor tubes and the diameter of the interior accommodation sheath for the thermocouple are selected so that the ratio of volume evolving heat of reaction to heat-removing surface area is the same or only slightly different for temperature sensor tubes and working tubes.

The pressure drop should be equal for working tubes and temperature sensor tubes, based on the same GHSV. Pressure drop equalization for the temperature sensor tube can, for example, be effected by addition of crushed catalyst to the shaped catalyst bodies. This equalization is advantageously effected homogeneously over the entire length of the temperature sensor tubes. In addition, temperature sensor tubes can be filled as described in EP-A 873783.

To provide the catalyst charge in the catalyst tubes, it is possible, as mentioned above, to use only catalysts according to the invention which can be obtained as described (e.g. the ring-shaped catalyst bodies) or, for example, largely homogeneous mixtures of, for example, ring-shaped catalyst bodies which can be obtained as described and shaped bodies which have no active composition and are essentially inert in respect of the heterogeneously catalyzed partial gas-phase oxidation. Possible materials for such inert shaped bodies are, for example, porous or nonporous aluminum oxides, silicon dioxide, zirconium dioxide, silicon carbide, silicates such as magnesium silicate or aluminum silicate and/or steatite (e.g. of the type C220 from CeramTec, Germany).

The geometry of such inert diluent shaped bodies can in principle be any desired geometry, i.e. spheres, polygons, solid cylinders or, as in the case of, for example, ring-shaped catalyst bodies, rings, for example, are possible. Inert diluent shaped bodies used are frequently bodies whose geometry corresponds to the shaped catalyst bodies to be diluted therewith. However, it is also possible for the geometry of the shaped catalyst body to be changed along the catalyst charge or for shaped catalyst bodies of various geometries to be used in a largely homogeneous mixture. In a less preferred procedure, the active composition of the shaped catalyst body can also be changed along the catalyst charge.

Quite generally, the catalyst charge is, as mentioned above, advantageously configured so that the volume-based activity (i.e. the activity per unit volume) either remains constant or increases (continuously, abruptly or stepwise) in the flow direction of the reaction gas mixture.

A reduction in the volume-based activity can be achieved in a simple way by, for example, homogeneously diluting a basic amount of, for example, ring-shaped catalyst bodies produced uniformly according to the invention with inert diluent shaped bodies. The greater the proportion of the diluent shaped bodies, the lower the amount of active composition comprised in a particular volume of the charge and thus the catalyst activity. However, a reduction can also be achieved by changing the geometry of the shaped catalyst bodies which can be obtained according to the invention in such a way that the amount of active composition per unit volume of the reaction interior is smaller.

In the heterogeneously catalyzed gas-phase partial oxidations using ring-shaped all-active shaped catalyst bodies which can be produced as described is preferably configured either with only one type of all-active ring-shaped catalyst bodies over the entire length or is structured as follows. At the reactor inlet, an essentially homogeneous mixture of ring-shaped all-active catalyst bodies which can be obtained according to the invention and inert diluent shaped bodies (with both preferably having essentially the same geometry) is placed over a length of from 10 to 60%, preferably from 10 to 50%, particularly preferably from 20 to 40% and particularly preferably from 25 to 35% (i.e., for example, a length of from 0.70 to 1.50 m, preferably from 0.90 to 1.20 m), in each case of the total length of the catalyst charge, with the proportion by weight of the diluent shaped bodies (the densities of shaped catalyst bodies and of diluent shaped bodies generally differ only slightly) normally being from 5 to 40% by weight, or from 10 to 40% by weight, or from 20 to 40% by weight, or from 25 to 35% by weight. Subsequent to this first section of the charge, either a bed of the ring-shaped all-active catalyst body according to the invention which can be obtained as described diluted only to a small extent (compared to the first section) or, very particularly preferably, a sole (undiluted) bed of the same ring-shaped all-active catalyst body according to the invention which has also been used in the first section. Naturally, a constant dilution over the entire charge can also be selected. It is also possible for the first section to be charged only with a ring-shaped all-active catalyst body which can be obtained according to the invention and has a relatively low active composition density based on the volume it occupies and the second section to be charged with a ring-shaped all-active catalyst body which can be obtained according to the invention and has a high active composition density based on the volume it occupies (e.g. 6.5 mm×3 mm×4.5 mm [E×H×I] in the first section and 5×2×2 mm in the second section).

Overall, the catalyst charge, the reaction gas starting mixture, the space velocity and the reaction temperature in a partial oxidation to prepare acrolein or methacrolein carried out using the (e.g. ring-shaped) shaped catalyst bodies according to the invention which can be obtained as described as catalysts are generally selected so that a conversion of the organic compound to be partially oxidized (propene, isobutene, tert-butanol or the methyl ether thereof) of at least 90 mol %, or at least 92 mol %, preferably at least 94 mol %, is obtained in a single pass of the reaction gas mixture through the catalyst charge. The selectivity of acrolein or methacrolein formation will normally be ≥80 mol %, or ≥85 mol %. Naturally, the lowest possible hot spot temperatures are sought here.

Finally, it may be stated that ring-shaped all-active catalyst bodies according to the invention which can be obtained as described also have an advantageous fracture behavior on charging the reactor.

The start-up of a catalyst charge (fixed catalyst bed) comprising fresh geometric shaped catalyst bodies which can be obtained according to the invention can be carried out as described, for example, in DE-A 103 37 788 or in DE-A 102009047291.

The activation of geometric shaped catalyst bodies which can be obtained according to the invention can be accelerated by carrying it out at an essentially constant conversion with an increased space velocity of the reaction gas starting mixture over the catalyst charge.

Furthermore, multimetal oxide compositions of the general stoichiometry I which can be obtained according to the invention and catalysts having these as active composition are quite generally suitable for catalyzing the gas-phase partial oxidation of an alkanol, alkanal, alkene, alkane and alkenal comprising from 3 to 6 (i.e. 3, 4, 5 or 6) carbon atoms to form, for example, olefinically unsaturated aldehydes and/or carboxylic acids and also the corresponding nitriles and for gas-phase catalytic oxidative dehydrogenations of the above-mentioned organic compounds comprising 3, 4, 5 or 6 carbon atoms.

The industrial production of ring-shaped all-active catalyst bodies according to the invention is advantageously carried out as described in the German first publications DE-A 102008040093 and DE-A 102008040094.

The present application therefore comprises, in particular, the following embodiments according to the invention:

1. Mo-, Bi- and Fe-comprising multimetal oxide compositions of the general stoichiometry I, $$Mo_{12}Bi_aCo_bFe_cK_dSi_eO_x \tag{I},$$

where the variables have the following meanings:
a=0.5 to 1,
b=7 to 8.5,
c=1.5 to 3.0,
d=0 to 0.15,
e=0 to 2.5 and x=a number which is determined by the valence and abundance of the elements other than oxygen in I
and fulfill the following conditions:

$$12-b-1.5 \cdot c = A,$$

and $$0.5 \leq A \leq 1.5; \quad \text{condition 1}$$

$$0.2 \leq a/A \leq 1.3; \text{ and} \quad \text{condition 2}$$

$$2.5 \leq b/c \leq 9. \quad \text{condition 3}$$

2. A multimetal oxide composition according to embodiment 1 whose stoichiometric coefficient d is from 0.04 to 0.1.
3. A multimetal oxide composition according to embodiment 1 or 2 whose stoichiometric coefficient d is from 0.05 to 0.08.
4. A multimetal oxide composition according to any of embodiments 1 to 3 whose stoichiometric coefficient e is from 0.5 to 2.
5. A multimetal oxide composition according to any of embodiments 1 to 4 whose stoichiometric coefficient e is from 0.8 to 1.8.
6. A multimetal oxide composition according to any of embodiments 1 to 5 whose stoichiometric coefficient e is from 1 to 1.6.
7. A multimetal oxide composition according to any of embodiments 1 to 6 which fulfils condition 1, $0.5 \leq A \leq 1.25$.
8. A multimetal oxide composition according to any of embodiments 1 to 7 which fulfils the condition 1, $0.5 \leq A \leq 1$.
9. A multimetal oxide composition according to any of embodiments 1 to 8 which fulfils the condition 2, $0.3 \leq a/A \leq 1.2$.
10. A multimetal oxide composition according to any of embodiments 1 to 9 which fulfils the condition 2, $0.4 \leq a/A \leq 1.2$.
11. A multimetal oxide composition according to any of embodiments 1 to 10 which fulfils the condition 2, $0.5 \leq a/A \leq 1.2$.
12. A multimetal oxide composition according to any of embodiments 1 to 11 which fulfils the condition 3, $3 \leq b/c \leq 9$.
13. A multimetal oxide composition according to any of embodiments 1 to 12 which fulfils the condition 3, $3 \leq b/c \leq 7$.
14. A multimetal oxide composition according to any of embodiments 1 to 13 which fulfils the condition 3, $3 \leq b \leq 5$.
15. A multimetal oxide composition according to any of embodiments 1 to 14 whose specific surface area is from 2 to 20 m$^2$/g.
16. A multimetal oxide composition according to any of embodiments 1 to 15 whose specific surface area is from 2 to 15 m$^2$/g.
17. A multimetal oxide composition according to any of embodiments 1 to 16 whose specific surface area is from 3 to 10 m$^2$/g.
18. A multimetal oxide composition according to any of embodiments 1 to 17 whose specific surface area is from 4 to 8 m$^2$/g.
19. A multimetal oxide composition according to any of embodiments 1 to 18 whose total pore volume is from 0.1 to 1 cm$^3$/g.
20. A multimetal oxide composition according to any of embodiments 1 to 19 whose total pore volume is from 0.1 to 0.8 cm$^3$/g.
21. A multimetal oxide composition according to any of embodiments 1 to 20 whose total pore volume is from 0.1 to 0.5 cm$^3$/g.
22. A multimetal oxide composition according to any of embodiments 1 to 21 whose total pore volume is from 0.2 to 0.4 cm$^3$/g.
23. A multimetal oxide composition according to any of embodiments 1 to 22, wherein the contribution of pores having a pore radius of $\leq 0.1$ μm to the total pore volume is $\leq 0.05$ cm$^3$/g.
24. A multimetal oxide composition according to any of embodiments 1 to 23, wherein the contribution of pores having a pore radius in the range from 0.2 to 0.4 μm to the total pore volume is $\geq 70\%$ by volume, based on the total pore volume.
25. A multimetal oxide composition according to any of embodiments 1 to 24, wherein the contribution of pores having a pore radius in the range from 0.2 to 0.4 μm to the total pore volume is $\geq 75\%$ by volume, based on the total pore volume.
26. A multimetal oxide composition according to any of embodiments 1 to 25, wherein the contribution of pores having a pore radius in the range from 0.2 to 0.4 μm to the total pore volume is $\geq 85\%$ by volume, based on the total pore volume.
27. A multimetal oxide composition according to any of embodiments 1 to 26, wherein the contribution of pores having a pore radius in the range from 0.2 to 0.4 μm to the total pore volume is $\geq 90\%$ by volume, based on the total pore volume.
28. A multimetal oxide composition according to any of embodiments 1 to 27, wherein the contribution of pores having a pore radius in the range from 0.2 to 0.4 μm to the total pore volume is $\geq 95\%$ by volume, based on the total pore volume.
29. A multimetal oxide composition according to any of embodiments 1 to 28, wherein a plot of the pore diameter thereof in μm on the abscissa and the logarithm of the differential contribution in cm$^3$/g of the respective pore diameter to the total pore volume in cm$^3$/g on the ordinate gives a monomodal distribution curve.
30. A coated catalyst comprising a shaped support body and a coating of at least one multimetal oxide composition according to any of embodiments 1 to 29 present on the outer surface of the shaped support body.
31. A coated catalyst according to embodiment 30, wherein the shell of the at least one multimetal oxide composition has a thickness of from 10 to 1000 μm.
32. A coated catalyst according to embodiment 30 or 31, wherein the shell of the at least one multimetal oxide composition has a thickness of from 100 to 700 μm.
33. A coated catalyst according to any of embodiments 30 to 32, wherein the shell of the at least one multimetal oxide composition has a thickness of from 300 to 500 μm.
34. A coated catalyst according to any of embodiments 30 to 33 whose shaped support body is a sphere, a solid cylinder or a hollow cylinder.
35. A coated catalyst according to embodiment 34 whose shaped support body is a sphere having a diameter of from 1 to 8 mm.
36. A coated catalyst according to embodiment 34 whose shaped support body is a cylinder having a length of from 2 to 10 mm and an external diameter of from 4 to 10 mm.
37. A coated catalyst according to embodiment 34 whose shaped support body is a ring having a wall thickness of from 1 to 4 mm, a length of from 2 to 10 mm and an external diameter of from 4 to 10 mm.

38. A coated catalyst according to embodiment 37 whose shaped support body is a ring having a wall thickness of from 1 to 2 mm, a length of from 3 to 6 mm and an external diameter of from 4 to 8 mm.
39. A coated catalyst according to embodiment 37 whose shaped support body is a ring having a wall thickness of from 1 to 2 mm, a length of from 2 to 4 mm and an external diameter of from 4 to 8 mm.
40. A coated catalyst according to any of embodiments 30 to 39, wherein the material of the shaped support body is aluminum oxide, silicon dioxide, a silicate, silicon carbide, zirconium dioxide, thorium dioxide or steatite.
41. An all-active shaped catalyst body whose active composition is at least one multimetal oxide according to any of embodiments 1 to 29.
42. An all-active shaped catalyst body according to embodiment 41 which has the geometry of a sphere, a cylinder or a ring.
43. An all-active shaped catalyst body according to embodiment 42 which has the geometry of a sphere having a diameter of from 2 to 10 mm.
44. An all-active shaped catalyst body according to embodiment 43 whose sphere diameter is from 4 to 8 mm.
45. An all-active shaped catalyst body according to embodiment 42 which has the geometry of a cylinder having a length of from 2 to 10 mm and an external diameter of from 2 to 10 mm.
46. An all-active shaped catalyst body according to embodiment 45, wherein the length is from 2 to 8 mm and the external diameter is from 2 to 8 mm.
47. An all-active shaped catalyst body according to embodiment 42 which has the geometry of a ring having a wall thickness of from 1 to 3 mm, a length of from 2 to 10 mm and an external diameter of from 2 to 10 mm.
48. An all-active shaped catalyst body according to embodiment 47 whose length is from 2 to 8 mm and whose external diameter is from 3 to 8 mm.
49. An all-active shaped catalyst body according to embodiment 47 whose length is from 3 to 8 mm and whose external diameter is from 3 to 8 mm.
50. An all-active shaped catalyst body according to any of embodiments 47 to 49, wherein the ratio of length to external diameter is from 0.3 to 0.7.
51. An all-active shaped catalyst body according to embodiment 50, wherein the ratio of length to external diameter is from 0.4 to 0.6.
52. An all-active shaped catalyst body according to any of embodiments 47 to 51, wherein the ratio of internal diameter to external diameter is from 0.3 to 0.7.
53. An all-active shaped catalyst body according to embodiment 52, wherein the ratio of internal diameter to external diameter is from 0.4 to 0.7.
54. An all-active shaped catalyst body according to embodiment 47 whose ring geometry having an External diameter×Length×Internal diameter is a ring geometry selected from the group consisting of 5 mm×2 mm×2 mm, 5 mm×3 mm×2 mm, 5 mm×3 mm×3 mm, 5.5 mm×3 mm×3.5 mm, 6 mm×3 mm×4 mm, 6.5 mm×3 mm×4.5 mm, 7 mm×3 mm×5 mm, 7 mm×7 mm×3 mm, 7 mm×3 mm×4 mm and 7 mm×7 mm×4 mm.
55. A process for preparing a multimetal oxide composition according to any of embodiments 1 to 29, wherein a finely divided intimate dry mix is produced from sources of elemental constituents of the multimetal oxide composition and this mixture is calcined at temperatures in the range from 350 to 650° C.
56. A process according to embodiment 55, wherein the calcination is carried out under inert gas, under a mixture of molecular oxygen and an inert gas, under a reducing atmosphere or under reduced pressure.
57. A process according to embodiment 56, wherein the calcination is carried out in air.
58. A process according to any of embodiments 55 to 57, wherein the sources are mixed with one another in the form of solutions and/or suspensions and the resulting wet mixture M is dried to give the finely divided intimate dry mix.
59. A process according to embodiment 58, wherein the solvent and/or suspension medium is an aqueous solution.
60. A process according to embodiment 58 or 59, wherein only solutions and/or colloidal solutions are used as sources.
61. A process according to embodiment 60, wherein one source is an aqueous solution A which comprises the starting compounds of the elements Co, Fe and Bi in dissolved form and has a pH of from ≤3 to ≥−2.
62. A process according to embodiment 60 or 61, wherein one source is an aqueous solution B which comprises the starting compounds of the elements K and Mo in dissolved form and has a pH of from ≤6.5 to ≥3.
63. A process according to any of embodiments 60 to 62, wherein one source is an aqueous silica sol.
64. A process according to any of embodiments 55 to 63, wherein, in the production of the finely divided intimate dry mix, an aqueous solution A which comprises starting compounds of the elements Co, Fe and Bi in dissolved form and has a pH of from ≤3 to ≥−2 is mixed with an aqueous solution B which comprises starting compounds of the elements K and Mo in dissolved form and has a pH of from ≤6.5 to ≥3 and the resulting aqueous mixture is mixed into an aqueous silica sol to give an aqueous mixture M.
65. A process according to embodiment 64, wherein the aqueous solution A is stirred into the aqueous solution B.
66. A process according to embodiment 65, wherein the stirring-in is carried out at a temperature of from ≤80° C. to ≥0° C.
67. A process according to embodiment 66, wherein the stirring-in is carried out at a temperature of from ≤70° C. to ≥0° C.
68. A process according to embodiment 66 or 67, wherein the stirring-in is carried out at a temperature of from ≤60° C. to ≥0° C.
69. A process according to any of embodiments 66 to 68, wherein the stirring-in is carried out at a temperature of from ≤40° C. to ≥0° C.
70. A process according to any of embodiments 64 to 69, wherein the ratio V of the total molar amount $n_1$ of $NH_3$ and $NH_4^+$ which is present if desired in the aqueous mixture of aqueous solution A and aqueous solution B to the total molar amount $n_2$ of Mo comprised in the same aqueous mixture, $V=n_1:n_2$, is ≤1.
71. A process according to embodiment 70, wherein 0≤V≤6/7.
72. A process according to any of embodiments 64 to 71, wherein the pH of the aqueous mixture of the aqueous solution A and the aqueous solution B is from ≤3 to ≥0.
73. A process according to any of embodiments 64 to 72, wherein the $SiO_2$ content of the aqueous silica sol is from 15 to 60% by weight.
74. A process according to any of embodiments 64 to 73, wherein the $SiO_2$ content of the aqueous silica sol is from 30 to 60% by weight.

75. A process according to any of embodiments 64 to 74, wherein the SiO$_2$ content of the aqueous silica sol is from 45 to 55% by weight.
76. A process according to any of embodiments 64 to 75, wherein the total content of Mo, Co, Fe, Bi and Si in the aqueous mixture M is from 5 to 25% by weight, based on the amount of water comprised in the aqueous mixture M.
77. A process according to embodiment 76, wherein the total content of Mo, Co, Fe, Bi and Si in the aqueous mixture M is from 8 to 20% by weight, based on the amount of water comprised in the aqueous mixture M.
78. A process according to any of embodiments 64 to 77, wherein the pH of the aqueous mixture M is ≤3.
79. A process according to embodiment 78, wherein the pH of the aqueous mixture M is from ≥0 to ≤2.
80. A process according to any of embodiments 64 to 79, wherein the proportion AT of Co which is dissolved in the aqueous medium of the aqueous mixture M is ≤60% of the total amount of Co comprised in the aqueous mixture M.
81. A process according to embodiment 80, wherein AT is ≤50%.
82. A process according to embodiment 80 or 81, wherein 15%≤AT≤40%.
83. A process according to any of embodiments 58 to 82, wherein drying is carried out by spray drying.
84. A process according to embodiment 83, wherein the spray drying of the aqueous mixture M is carried out by spraying this mixture into a hot stream of gas whose inlet temperature is from 250 to 450° C.
85. A process according to any of embodiments 55 to 84, wherein the intimate dry mix is, if desired with addition of shaping aids, shaped to form shaped bodies having a regular or irregular geometry before calcination.
86. A process according to embodiment 85, wherein shaping is carried out by tabletting.
87. A process according to embodiment 85 or 86, wherein graphite is added as shaping aid.
88. A process according to any of embodiments 85 to 87, wherein the shaped body has the geometry of a ring.
89. A process according to embodiment 88, wherein the ring has an external diameter of from 2 to 10 mm, a height of from 2 to 10 mm and a wall thickness of from 1 to 3 mm.
90. A process according to embodiment 89, wherein the ring has an external diameter of from 2 to 8 mm and a height of from 2 to 8 mm.
91. A process according to embodiment 89 or 90, wherein the ring has an external diameter of from 3 to 8 mm and a height of from 3 to 8 mm.
92. A process according to any of embodiments 88 to 91, wherein the lateral compressive strength LCS of the ring-shaped body fulfils the relationship 12 N≤LCS≤35 N.
93. A process according to embodiment 92, wherein the lateral compressive strength fulfils the relationship 15 N≤LCS≤30 N.
94. A process according to embodiment 92 or 93, wherein the lateral compressive strength fulfils the relationship 19 N≤LCS≤30 N.
95. A process according to any of embodiments 55 to 94, wherein a temperature of 600° C. is not exceeded during the calcination.
96. A process according to any of embodiments 55 to 95, wherein a temperature of 550° C. is not exceeded during the calcination.
97. A process according to any of embodiments 55 to 96, wherein a temperature of 500° C. is not exceeded during the calcination.
98. A process according to any of embodiments 55 to 97, wherein a thermal treatment of the intimate dry mix is carried out at temperatures of from ≥120° C. to ≤350° C. before the calcination.
99. A process according to any of embodiments 55 to 98, wherein a thermal treatment of the intimate dry mix is carried out at temperatures of from ≥150° C. to ≤320° C. before the calcination.
100. A process according to any of embodiments 55 to 99, wherein a thermal treatment of the intimate dry mix is carried out at temperatures of from ≥220° C. to ≤290° C. before the calcination.
101. A process for the heterogeneously catalyzed partial gas-phase oxidation of an alkane, alkanol, alkanal, alkene and/or alkenal having from 3 to 6 carbon atoms over a catalyst bed, wherein the catalyst bed comprises at least one multimetal oxide composition according to any of embodiments 1 to 29.
102. A process for the heterogeneously catalyzed partial gas-phase oxidation of an alkane, alkanol, alkanal, alkene and/or alkenal having from 3 to 6 carbon atoms over a catalyst bed, wherein the catalyst bed comprises at least one catalyst according to any of embodiments 30 to 54.
103. A process for the heterogeneously catalyzed partial gas-phase oxidation of an alkane, alkanol, alkanal, alkene and/or alkenal having from 3 to 6 carbon atoms over a catalyst bed, wherein the catalyst bed comprises at least one product of a process according to any of embodiments 55 to 100.
104. A process according to any of embodiments 101 to 103 which is a process for the heterogeneously catalyzed partial gas-phase oxidation of propene to acrolein or of isobutene to methacrolein.
105. A process according to any of embodiments 101 to 103 which is a process for the ammoxidation of propene to acrylonitrile or a process for the ammoxidation of isobutene to methacrylonitrile.
106. The use of at least one multimetal oxide according to any of embodiments 1 to 29 or of at least one catalyst according to any of embodiments 30 to 54 or of at least one product of a process according to any of embodiments 55 to 100 for the catalysis of a process for the heterogeneously catalyzed partial gas-phase oxidation of an alkane, alkanol, alkanol, alkene and/or alkenal having from 3 to 6 carbon atoms over a catalyst bed.

EXAMPLES AND COMPARATIVE EXAMPLES

I. Process Employed for Producing Ring-Shaped all-Active Catalyst Bodies E1 to E4 and C1 to C7

1. Production of the Respective Aqueous Solution B

The amount M1 of deionized water indicated in each case in table 1 was placed in a stainless steel vessel (internal volume=10 dm$^3$) which was open to the atmosphere (1 atm, 1.01 bar), could be temperature-controlled and was equipped with an anchor stirrer and the water was heated to 60° C. while stirring (150 rpm). The amount M2 indicated in each case in table 1 of a 32% strength by weight aqueous solution of KOH in water, which had a temperature of 60° C., was subsequently added. After stirring for another 1 minute at 60° C., the amount M3 of ammonium heptamolybdate tetrahydrate (white crystals having a particle size d<1 mm, 55% by weight of Mo, 7.0-8.5% by weight of NH$_3$, max. 150 mg/kg of alkali metals, from H.C. Starck, D-38642 Goslar) indicated in each case in table 1 was stirred in a little at a time while maintaining the temperature at 60° C. and the resulting aqueous solution was stirred for another 20 minutes at 60° C. (150 rpm). The amount M4 of ammonium paratungstate (71% by weight, H.C. Starck, D-38642 Goslar) indicated in table 1 was subsequently added and the mixture was stirred for a further 20 minutes at 60° C. and 150 rpm. The pH of the resulting aqueous solution B was in the range from 4 to 6.

2. Production of the Respective Aqueous Solution A

The amount M5 indicated in table 1 of an aqueous cobalt (II) nitrate solution (12.4% by weight of Co, 27% by weight of nitrate ($NO_3^-$)), pH=1, produced by dissolving cobalt metal from MFT Metals & Ferro-Alloys Trading GmbH, D-41474 Viersen, purity >99.6% by weight of Co, <0.3% by weight of Ni, <100 mg/kg of Fe, <50 mg/kg of Cu in nitric acid) was in each case placed in a stainless steel vessel (internal volume=5 $dm^3$) which was open to the atmosphere (1 atm, 1.01 bar), could be temperature-controlled and was equipped with an anchor stirrer and the mixture was heated to 60° C. while stirring (150 rpm). While continuing to stir (150 rpm) and continuing to maintain the temperature at 60° C., the amount M6 of crystalline iron(III) nitrate nonahydrate (13.6% by weight of Fe, <0.4% by weight of alkali metals, <0.01% by weight of chloride, <0.02% by weight of sulphate, from Dr. Paul Lohmann GmbH, D-81857 Emmerthal) indicated in table 1 was in each case added and the mixture was stirred for another 10 minutes at 60° C. The amount M7 indicated in table 1 of an aqueous, nitric acid solution of bismuth nitrate having a temperature of 60° C. (10.8% by weight of Bi, 13% by weight of nitrate, produced by dissolving bismuth metal from Sidech S.A., BE-1495 Tilly, purity >99.997% by weight of Bi, <7 mg/kg of Pb, <5 mg/kg of each of Ni, Ag, Fe, <3 mg/kg of each of Cu, Sb and <1 mg/kg of Cd, Zn in nitric acid) was in each case added to the resulting aqueous solution and the mixture was stirred for another 10 minutes at 60° C. The pH of the resulting aqueous solution A was in each case in the range from −1 to 0.

3. Mixing of the Respective Aqueous Solution A with the Respective Aqueous Solution B The respective aqueous solution A having a temperature of 60° C. was introduced continuously over a period of 15 minutes by means of a peristaltic pump (type: BVP, manufacturer: Ismatec SA, Labortechnik-Analytik, Feldeggstraβe 6, CH-8152 Glattbrugg, setting: 320 scale divisions) into the respective aqueous solution B which had a temperature of 60° C. and was now being intensively stirred by means of an Ultra-Turrax (from Janke & Kunkel GmbH & Co. KG-IKA-Labortechnik, Janke & Kunkel-Str. 10, DE-79219 Staufen, shaft type: 550KR-G45 fine, shaft tube diameter: 25 mm, stator diameter: 45 mm, rotor diameter: 40 mm, setting: 5). The aqueous solution A was introduced at the level of the rotor of the Ultra-Turrax stirrer at a distance of about 0.5-1 cm from the outer edge of the rotor of the Ultra-Turrax stirrer. The aqueous suspension formed was stirred for another 15 minutes at 60° C.

4. Addition of a Silica Gel to Give the Respective Aqueous Mixture M

The amount M8 indicated in table 1 of a silica gel of type Ludox TM50 from Grace (24.4% by weight of Si, density: 1.29 g/$cm^3$, pH: 8.5 to 9.5, alkali metal content max. 0.5% by weight) which had been heated to 60° C. was then in each case added to the aqueous mixture obtained in each case in "3." and the mixture was then stirred for a further 15 minutes at 60° C. The pH of the resulting aqueous mixture M was in each case in the range from 1 to 2 (in the case of the all-active shaped catalyst bodies C1, C2, C3, C4, C6 and C7 and also E1 and E3) or in the range from 0 to 1 (in the case of the all-active shaped catalyst bodies E2, E4 and C5).

The solids content of the various resulting aqueous mixtures M (the term solid includes the composition which deposits as solid sediment in the centrifugation described below and is not additionally dried: centrifuge Universal 16 from Hettich, speed of rotation: 3000 rpm, centrifugation time: 10 min, use of centrifuge tubes having a fill volume of 100 ml, reference temperature: 60° C.) was, based on the weight of the respective aqueous mixture M, in the range from 20 to 40% by weight (in the case of the all-active shaped catalyst bodies C1, C2, C3, C4, C6 and C7 and also E1 and E3) or in the range from 40 to 60% by weight (in the case of the all-active shaped catalyst bodies E2, E4 and C5). The supernatant liquid comprised, based on the total amount of cobalt comprised in the respective aqueous mixture M, from 60 to 90% by weight of Co in dissolved form (in the case of the all-active shaped catalyst bodies C1, C2, C3, C4, C6 and C7 and also E1 and E3) or from 40 to 60% by weight of Co in dissolved form (in the case of the all-active shaped catalyst bodies E2, E4 and C5). The separation of sediment and supernatant was in each case effected by decantation.

5. Spray Drying of the Respective Aqueous Mixture M

The respective aqueous mixture (suspension) M which had in each case been stirred further (including during spray drying) at 60° C. by means of the anchor stirrer (150 rpm) was spray dried in a Mobile Minor™ 2000 (MM-I) spray dryer from Niro A/S, Gladsaxevej 305, 2860 Søborg, Denmark, provided with a centrifugal atomizer of the type F01A and an atomizer disk of the type SL24-50 in a cocurrent of hot air (gas inlet temperature: 350±10° C., gas outlet temperature: 140±5° C.) over a period of from 90 to 140 minutes. The proportion which had not yet been spray dried was continually stirred further at 60° C. The setting of the speed of rotation of the atomizer disk was 25 000 rpm. This gave in each case about 700 g (in the case of the all-active shaped catalyst bodies C1, C2, C3, C4, C6 and C7 and also E1 and E3) or about 1100 g (in the case of the all-active shaped catalyst bodies E2, E4 and C5) of orange-brown spray-dried powder. The residual moisture contents of the various spray-dried powders (residual moisture determination by means of microwaves) were in the range from 3 (in the case of the all-active shaped catalyst body E3) to 7.7% by weight (in each case based on the total weight of the respective spray-dried powder). The loss on ignition of the various spray-dried powders (ignited for 3 h at 600° C. (powder temperature) under static air) was in all cases <35% by weight.

A representative particle diameter distribution of spray-dried powder (dispersion pressure=2 bar absolute) with $d_{10}$=9 μm, $d_{50}$=22 μm and $d_{90}$=39 μm is shown in FIG. 1 (for the case of the all-active shaped catalyst body B3). The abscissa shows the respective particle diameter (μm) on a logarithmic scale and the associated ordinate shows the percentage by volume of the spray-dried powder (based on its total volume) which comprises particles of the respective diameter and particles of a smaller diameter (% by volume).

TABLE 1

| All-active shaped catalyst body | Weighed-in stoichiometry in the aqueous mixture M | M1 [g] | M2 [g] | M3 [g] | M4 [g] | M5 [g] | M6 [g] | M7 [g] | M8 [g] |
|---|---|---|---|---|---|---|---|---|---|
| E1 | $Bi_{0.6}Mo_{12}Co_{8.0}Fe_{2.0}Si_{1.6}K_{0.08}$ | 4750 | 2.65 | 568.53 | 0 | 1032.68 | 223.06 | 315.33 | 50.2 |
| E2 | $Bi_{0.6}Mo_{12}Co_{8.0}Fe_{2.0}Si_{1.6}K_{0.08}$ | 2375 | 3.98 | 852.80 | 0 | 1549.02 | 334.60 | 473.00 | 75.03 |
| E3 | $Bi_{0.6}Mo_{12}Co_{8.4}Fe_{2.07}Si_{1.6}K_{0.08}$ | 4750 | 2.65 | 568.53 | 0 | 1084.31 | 230.87 | 315.33 | 50.02 |
| E4 | $Bi_{0.6}Mo_{12}Co_{8.4}Fe_{2.07}Si_{1.6}K_{0.08}$ | 2375 | 3.98 | 852.80 | 0 | 1626.47 | 346.31 | 473.00 | 75.03 |
| C1 | $Bi_{0.6}Mo_{12}Co_{8.7}Fe_{2.3}Si_{1.6}K_{0.08}$ | 4750 | 2.65 | 568.53 | 0 | 1123.04 | 256.52 | 315.33 | 50.02 |
| C2 | $Bi_{0.1}Mo_{12}Co_{8.0}Fe_{2.0}Si_{1.6}K_{0.08}$ | 4750 | 2.65 | 568.53 | 0 | 1032.68 | 223.06 | 52.56 | 50.02 |
| C3 | $Bi_{2.0}Mo_{12}Co_{8.0}Fe_{2.0}Si_{1.6}K_{0.08}$ | 4750 | 2.65 | 568.53 | 0 | 1032.68 | 223.06 | 1051.11 | 50.02 |
| C4 | $Bi_{0.6}Mo_{12}Co_{7.0}Fe_{3.0}Si_{1.6}K_{0.08}$ | 4750 | 2.65 | 568.53 | 0 | 903.60 | 334.60 | 315.33 | 50.02 |
| C5 | $Bi_{0.6}Mo_{12}Co_{7.0}Fe_{3.0}Si_{1.6}K_{0.08}$ | 2375 | 3.98 | 852.80 | 0 | 1355.39 | 501.89 | 473.00 | 75.03 |
| C6 | $Bi_{0.6}Mo_{12}Co_{4.6}Fe_{4.6}Si_{1.6}K_{0.08}$ | 4750 | 2.65 | 568.53 | 0 | 593.79 | 513.05 | 315.33 | 50.02 |
| C7 | $Bi_{0.6}Mo_{12}Co_{8.4}Fe_{2.07}Si_{1.6}W_{0.5}K_{0.08}$ | 4750 | 2.65 | 568.53 | 35.17 | 1084.31 | 230.87 | 315.33 | 50.02 |

6. Production of Ring-Shaped all-Active Catalyst Precursor Bodies (in N$_2$ Atmosphere)

1% by weight of finely divided graphite TIMREX T44 from Timcal Ltd., CH-6743 Bodio (cf. WO 2008/087116), based on the weight of the spray-dried powder, was homogeneously mixed into the respective spray-dried powder in a tumble mixer (wheel diameter: 650 mm, drum volume: 5 l, speed of rotation: 30 rpm, mixing time: 30 min). The resulting homogeneous mixture was compacted at a pressing pressure of 9 bar in a laboratory calender having 2 contrarotating steel rollers (roller diameter: 10 cm; roller length used for intermediate compaction: 13.5 cm: speed of rotation of the rollers: 10 rpm) and then subsequently pressed through a sieve having square mesh openings (edge length=0.8 mm). A further 2.5% by weight of the same finely divided graphite, based on the weight of the respective spray-dried powder which had been coarsened as described, was mixed into the coarsened spray-dried powder in the above-described tumble mixer (30 rpm, 30 min mixing time). The finely divided intimate dry mix obtained was subsequently compacted (tabletted) as described in DE-A 102008040093 by means of a Kilian retabletting machine (9× tabletting machine) model S100 (from Kilian, D-50735 Cologne) under a nitrogen atmosphere and an ambient temperature of 25° C. to form ring-shaped all-active catalyst precursor bodies having the geometry E×H×I=5 mm×3 mm×2 mm, a lateral compressive strength in the range from 19 N to 30 N (in the case of the all-active shaped catalyst body E3=30 N) and a mass of 119±2 mg. The pressing force was from 3.0 to 3.5 kN and the fill height was from 7.5 to 9 mm.

7. Thermal Pretreatment and Calcination of the Respective Ring-Shaped all-Active Catalyst Precursor Bodies For the final thermal treatment, 1000 g of the all-active shaped catalyst precursor bodies produced in each case were applied uniformly to 4 meshes having a square area of in each case 150 mm×150 mm and arranged on one another (bed height: 15 mm) in a convection shaft furnace (from Nabertherm; Oven model S60/65A) through which 4500 standard l/h of previously dried air (which had an inlet temperature of 140° C.) flowed (the convection furnace was located in an environment having a temperature of 25° C.). While maintaining the air stream (including its inlet temperature), the temperature in the convection shaft furnace was varied as follows (the temperatures reported are the temperature in the respective loose material applied; this was determined by means of 4 thermocouples which were in each case located at the geometric middle of the 4 meshes in the center of the loose material applied to the respective mesh; one of the thermocouples provided the actual value for regulating the temperature of the convection shaft furnace; the other thermocouples confirmed that the temperatures were identical within ±0.1° C.). The temperature increases were essentially linear over time. The samples were heated from 25° C. to 130° C. over a period of 72 minutes. This temperature was maintained for 72 minutes and then increased to 190° C. over a period of 36 minutes. The 190° C. was maintained for 72 minutes before the temperature was increased to 220° C. over a period of 36 minutes. The 220° C. was maintained for 72 minutes before the temperature was increased to 265° C. over a period of 36 minutes. The 265° C. was maintained for 72 minutes before the temperature was increased to 380° C. over a period of 93 minutes. The 380° C. was maintained for 187 minutes before the temperature was increased to 430° C. over a period of 93 minutes. The 430° C. was maintained for 187 minutes before the temperature was increased over a period of 93 minutes to the final calcination temperature of 500° C. This was maintained for 467 minutes. The samples were then cooled to 25° C. over a period of 12 hours. For this purpose, both the heating of the convection shaft furnace and the preheating of the stream of air were switched off (the air flow of 4500 standard l/h was, however, maintained; the inlet temperature of the stream of air was then 25° C.). The specific BET surface areas of the resulting ring-shaped all-active catalyst bodies were in the range from 4 to 8 m$^2$/g (in the case of the ring-shaped all-active catalyst body E3, the specific BET surface area was 7.6 m$^2$/g). The graphite content of the resulting ring-shaped all-active shaped catalyst bodies was 2.4% by weight (based on their total weight). Correspondingly, the comparative shaped catalyst bodies CK1-1 of WO 2010/066645 have a content of the graphite used for their production in that document of 3.45% by weight. The ring-like multimetal oxide all-active catalysts II of DE 102009047291 A1 analogously have a graphite content of 3.8% by weight. If they are produced using the graphite Timrex T44 from Timcal AG in the same proportions by weight instead of the graphite Asbury 3160, the remaining graphite content is only 1.4% by weight. The graphite content of the ring-shaped all-active shaped catalyst bodies from section B) of the examples and comparative examples of DE 102007004961 A1 is in all cases in the range from 1 to 4.5% by weight. When Asbury 3160 is used as graphite in the production of the all-active shaped catalyst bodies in this section B), the graphite content of the resulting all-active shaped catalyst body is 3.8% by weight. When Timrex 44 is used as graphite in this section B), the graphite content of the resulting all-active shaped catalyst bodies is 1.4% by weight.

Figure 2:
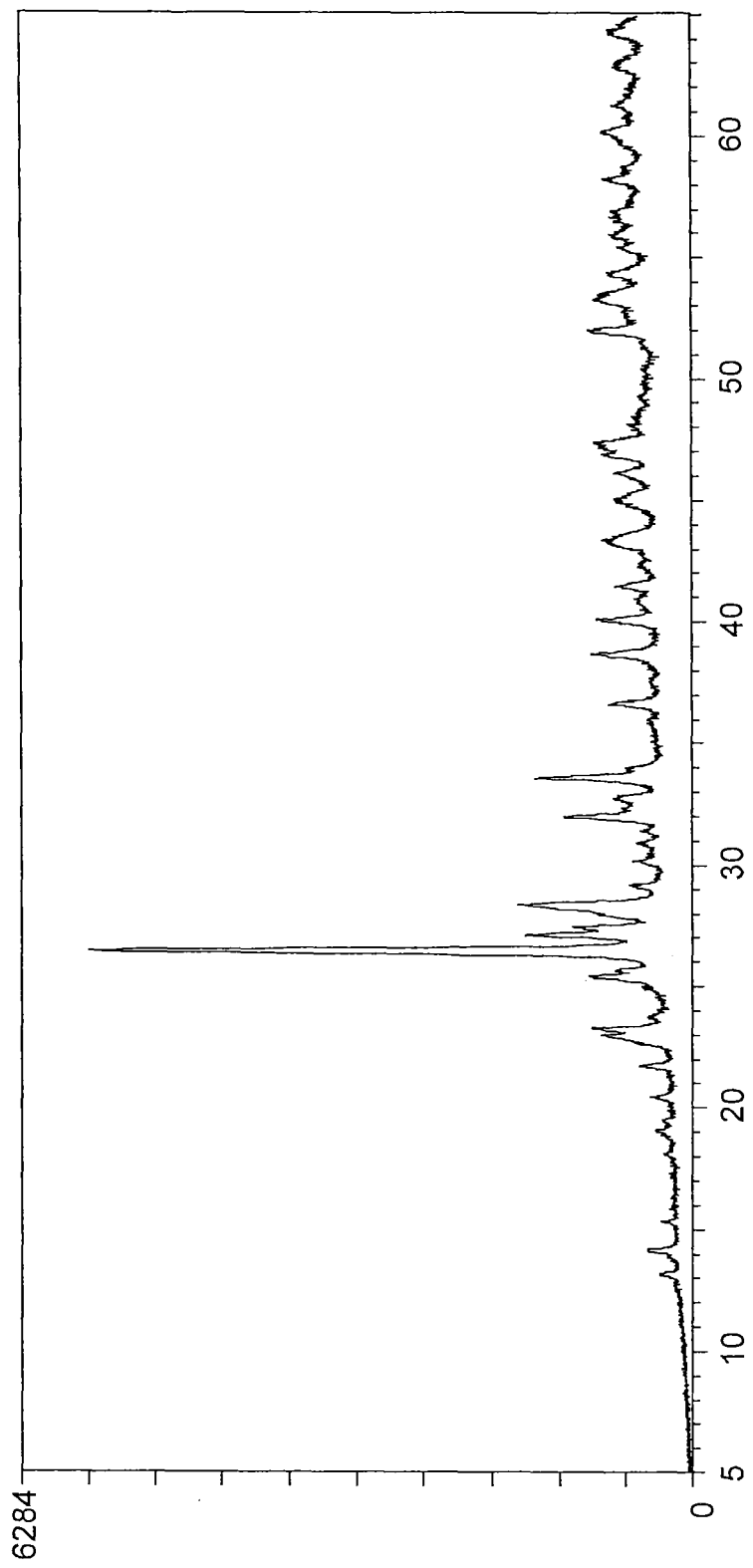
FIG. 2 shows a representative XRD pattern for the example of the all-active shaped catalyst body E3.

FIG. 2 shows a representative XRD pattern for the example of the all-active shaped catalyst body E3. The abscissa shows the diffraction angle on the 2Θ scale (2 theta scale) and the ordinate shows the absolute intensity of the diffracted X-radiation.

Figure 3:
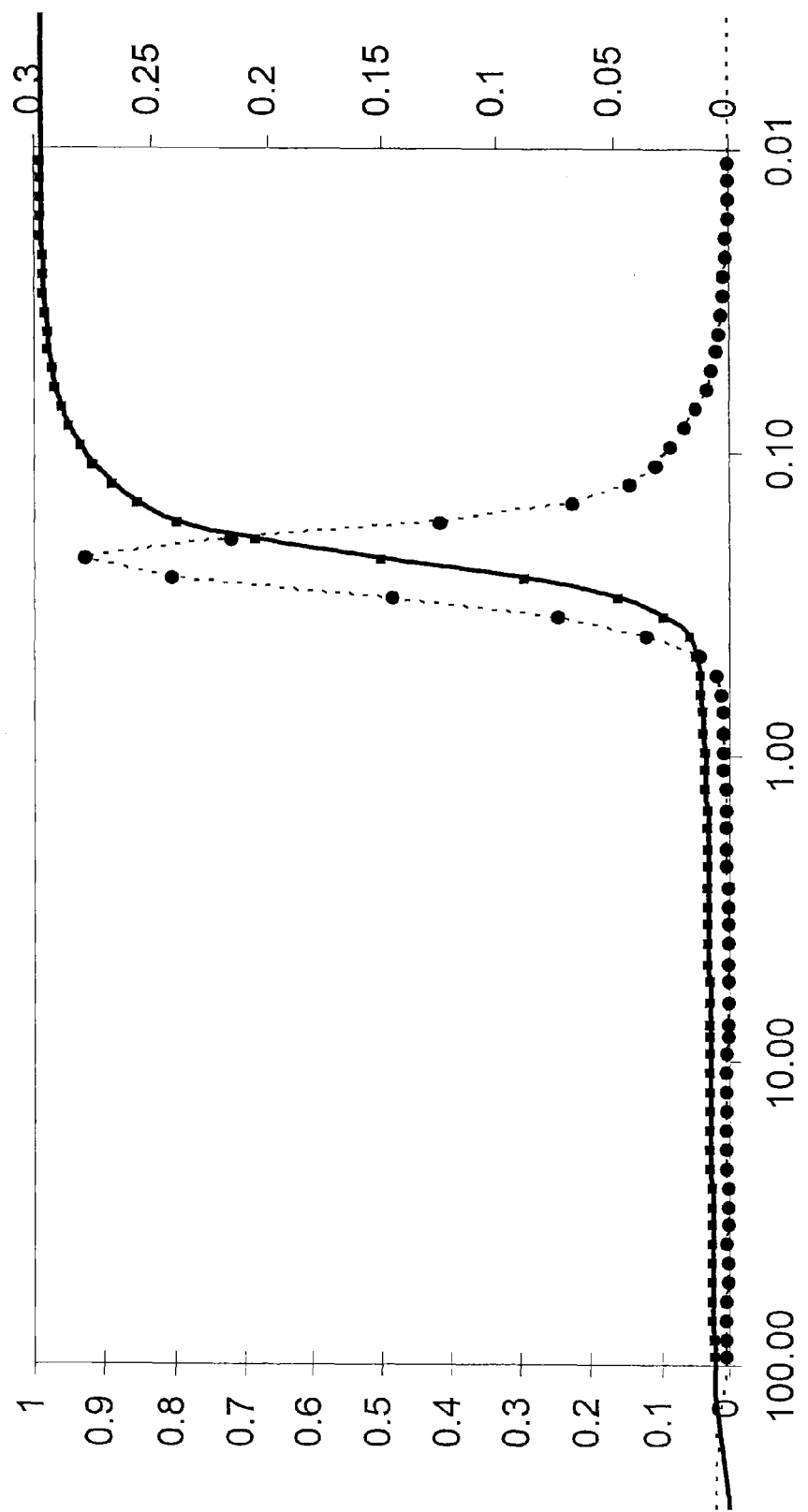
FIG. 3 shows a representative pore distribution, likewise for the example of the all-active shaped catalyst body E3.

FIG. 3 shows a representative pore distribution, likewise for the example of the all-active shaped catalyst body E3. The pore diameter in μm is plotted on the abscissa. The logarithm of the differential contribution in cm³/g of the respective pore diameter to the total pore volume/g is shown on the left-hand ordinate. The maximum indicates the pore diameter having the greatest contribution to the total pore volume. The integral over the individual contributions of the individual pore diameters to the total pore volume/g is plotted on the right-hand ordinate in cm³/g. The end point is the total pore volume/g.

Figure 4:
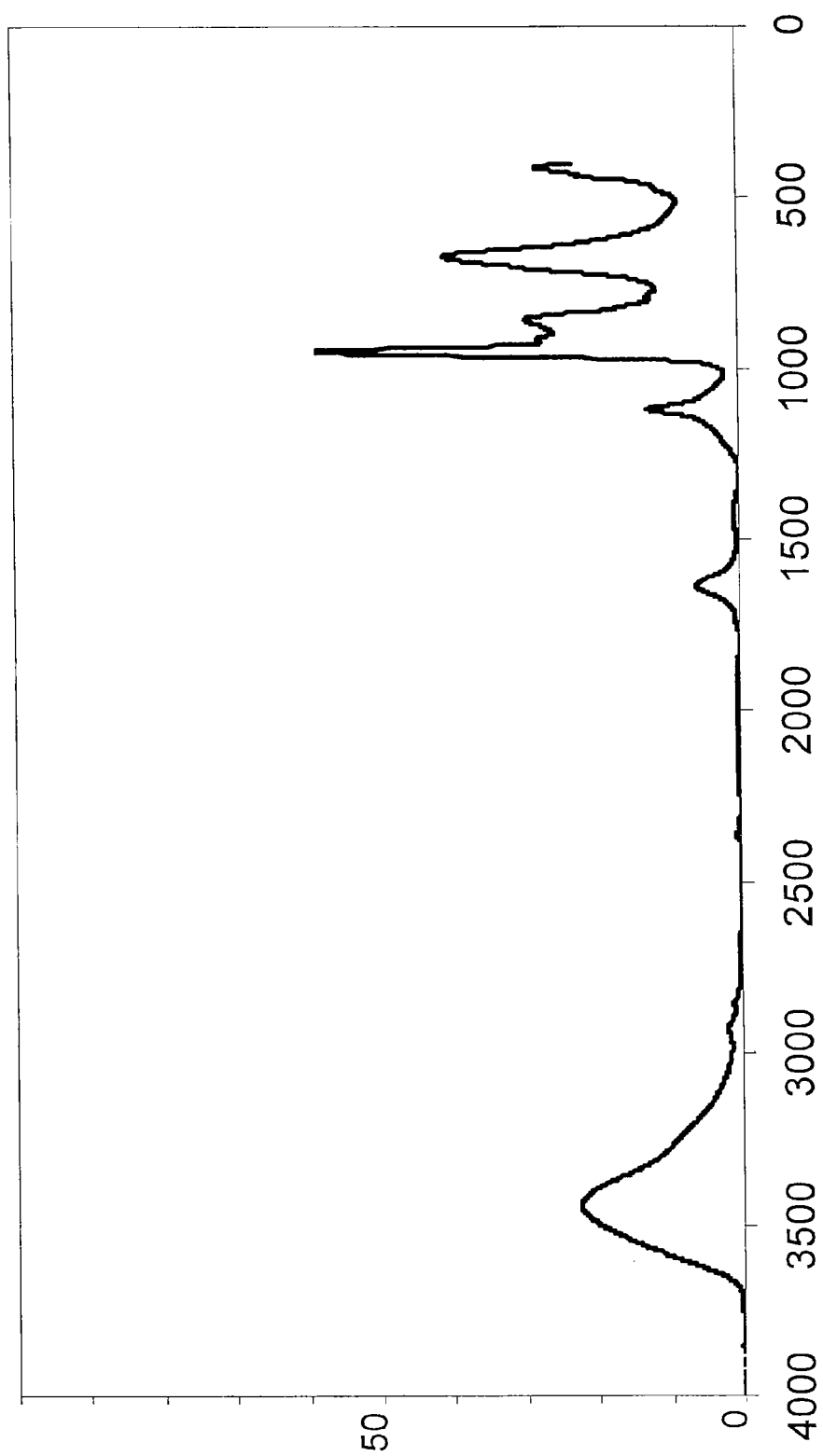
FIG. 4 shows a representative infrared transmission spectrum for the example of the all-active shaped catalyst body E3.

FIG. 4 shows a representative infrared transmission spectrum for the example of the all-active shaped catalyst body E3. The wave number in cm⁻¹ is plotted on the abscissa, and the transmission in % is plotted on the ordinate. The FTIR (Fourier Transformed Infrared) spectrometer Nicolet 6700 from Thermo Fisher Scientific was used as measuring instrument. The measurements were carried out after grinding of the respective all-active shaped catalyst body by means of a mortar and pestle (to particle sizes of <0.1 mm), on compacts subsequently produced from the respective ground powder with addition of finely divided KBr as IR-inactive diluent material. The associated measurement parameters were as follows: resolution=4 cm⁻¹; measurement range=4000 to 400 cm⁻¹; number of scans=32; type of measurement=transmission.

Figure 5:
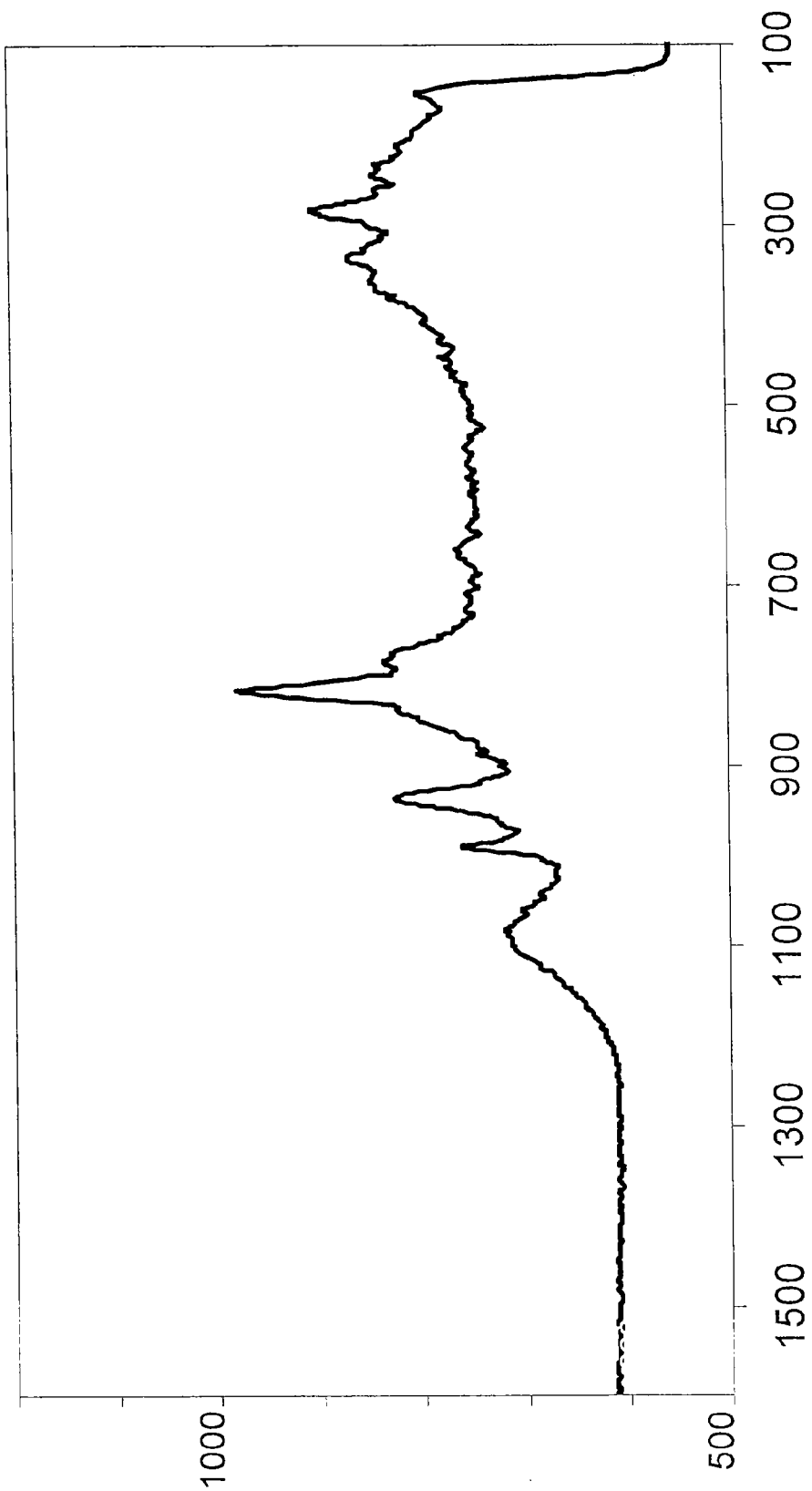
FIG. 5 shows a representative Raman spectrum for the example of the all-active shaped catalyst body E3.

FIG. 5 shows a representative Raman spectrum for the example of the all-active shaped catalyst body E3. The Raman shift in cm⁻¹ is plotted on the abscissa, and the associated Raman intensity is plotted on the ordinate. The Raman microscope Alpha 300 R from WiTec was used as measuring instrument. The measurement parameters in the Raman spectroscopy were as follows: Excitation wavelength of the laser: 532 nm; grid: 600 grids/ mm; number of accumulations: 100; integration time: 0.2 sec; lens used: Makroset with f=30 mm. The measurements were in each case carried out on the respective all-active shaped catalyst body ground to a particle size of <0.1 mm by means of a mortar and pestle.

Figure 6:
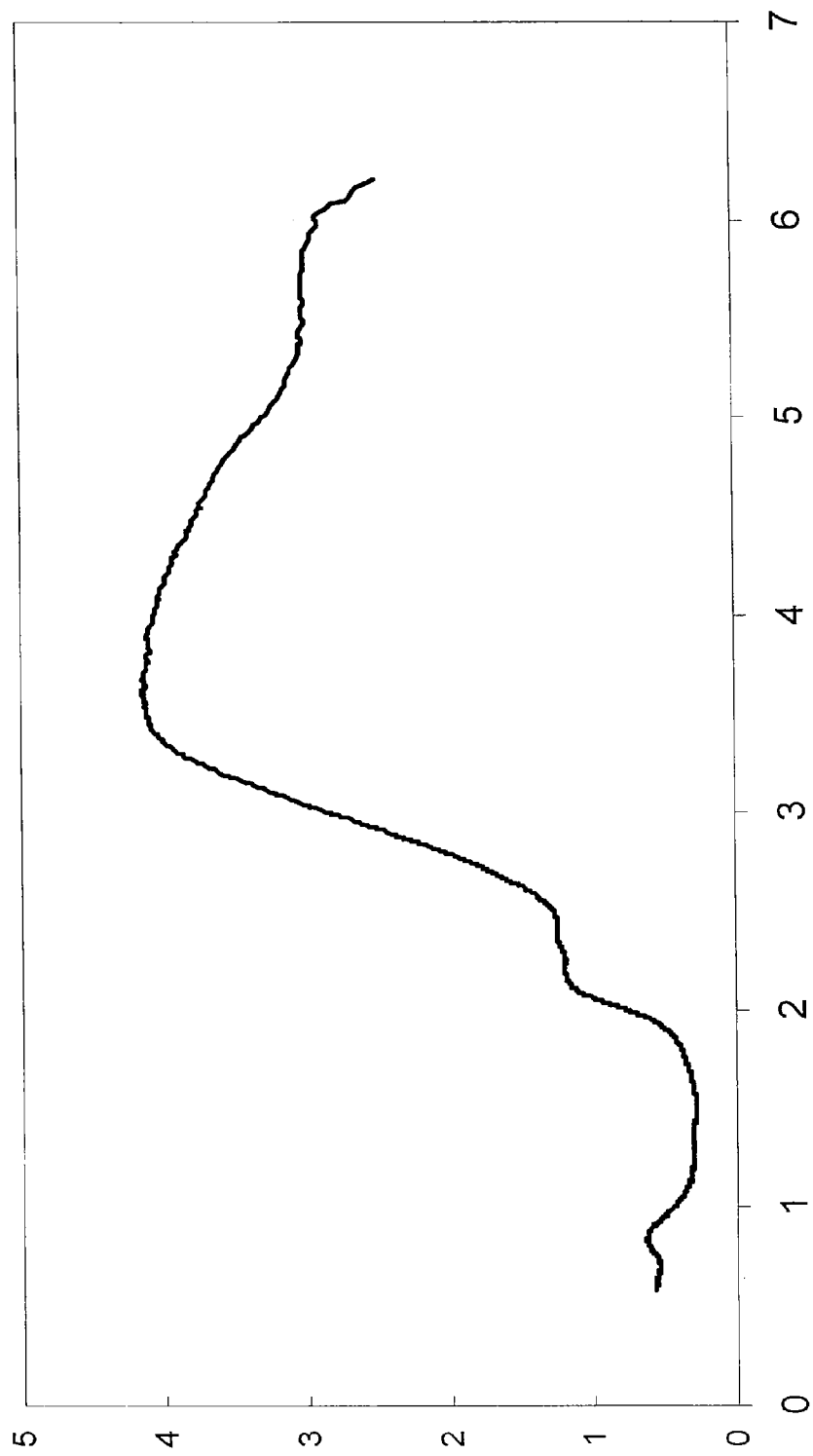
FIG. 6 shows a representative "pseudo" absorption spectrum in the wavelength range from 200 nm to 2126 nm for the example of the all-active shaped catalyst body E3.

FIG. 6 shows a representative "pseudo" absorption spectrum in the wavelength range from 200 nm to 2126 nm for the example of the all-active shaped catalyst body E3. The Kubelka-Munk absorption is plotted on the abscissa, and the energy of the electromagnetic waves with which the sample was irradiated is plotted on the ordinate in eV. The Kubelka-Munk formalism (cf. P. Kubelka, F. Munk, Z. Tech. Phys. 1931, 12, p. 593 ff) was utilized to transform the reflection measurement on the sample into a corresponding absorption spectrum. The UV/VIS/NIR spectrophotometer Lambda 900 with a 150 mm Ulbricht sphere and Spektralon white standard as reference from Labsphere was used as measuring instrument. The measurements were in each case carried out on the respective all-active shaped catalyst body ground to a particle size of <0.1 mm by means of a mortar and pestle. The measurement parameters in the UV/VIS/NIR spectroscopy were as follows: data interval: 1 nm; slit width: 2.0 nm/NIR auto; UV/VIS integration time: 0.44 sec/NIR 0.44 sec; measurement speed: 125 nm/min.

Table 2 shows the parameters A (condition 1), a/A (condition 2) and b/c (condition 3) determined for the various multimetal oxides of the ring-shaped all-active catalyst bodies.

TABLE 2

| All-active shaped catalyst body | A | a/A | b/c |
|---|---|---|---|
| E1 | 1 | 0.6 | 4.0 |
| E2 | 1 | 0.6 | 4.0 |
| E3 | 0.5 | 1.2 | 4.1 |
| E4 | 0.5 | 1.2 | 4.1 |
| C1 | −0.15 | −4 | 3.8 |
| C2 | 1 | 0.1 | 4.0 |
| C3 | 1 | 2 | 4.0 |
| C4 | 0.5 | 1.2 | 2.3 |
| C5 | 0.5 | 1.2 | 2.3 |
| C6 | 0.5 | 1.2 | 1.0 |
| C7 | 0.5 | 1.2 | 4.0 |

II. Catalysis of a Heterogeneously Catalyzed Partial Gas-Phase Oxidation of Propene to Acrolein (Main Product) and Acrylic Acid (by-Product) Using the Ring-Shaped all-Active Catalyst Bodies Produced in I.

A reaction tube (V2A steel, 12 mm external diameter, 3 mm wall thickness, 15 mm internal diameter, 120 cm length) was charged from the top downward (in the future flow direction of the reaction gas mixture) as follows:

Section 1: 30 cm length
40 g of steatite balls (Steatite C220 from CeramTec) having a diameter of from 1.5 to 2.0 mm as preliminary bed;

Section 2: 70 cm length
Catalyst charge comprising 100 g of the respective ring-shaped all-active catalyst produced in I.

The temperature of the reaction tube was in each case controlled by means of a salt melt (53% by weight of potassium nitrate, 40% by weight of sodium nitrite and 7% by weight of sodium nitrate) through which molecular nitrogen was bubbled and which had a salt bath temperature $T^{SB}$ of 320° C. The salt bath (the salt melt) was present in a cylindrical shell having an internal diameter of 15 nm. The cylindrical shell had the same length as the reaction tube. The latter was introduced from the top downward into the cylindrical shell in such a way that the two axes of symmetry coincided. The stream of nitrogen bubbled from below into the salt bath had a flow of 40 standard l/h (STP=1.01 bar, 0° C.). The heat losses of the salt bath to the surroundings were greater than the heat of reaction transferred to the salt bath by the tube reactor during the partial oxidation. The salt bath was therefore maintained at the temperature $T^{SB}$ (° C.) by means of electric heating. This ensured that the outer wall of the reaction tube always had the appropriate temperature $T^{SB}$ (° C.).

The reaction tube was supplied continuously with a reaction gas starting mixture having the following composition:
5% by volume of propene (polymer grade)
9.5% by volume of molecular oxygen and
85.5% by volume of molecular nitrogen.

The flow of the reaction gas starting mixture stream was in each case set so that the resulting propene conversion, based on a single pass of the reaction gas starting mixture through the reaction tube, at the salt bath temperature $T^{SB}$=320° C., was 95 mol %. The pressure at the inlet of the reaction tube was in all cases 1.2 bar absolute (a regulating valve was present at the outlet of the reaction tube to set the inlet pressure).

Table 3 shows the space velocity of propene PSV over the fixed catalyst bed (here in standard l of propene/(100 g of all-active shaped catalyst bodies·h), which was compatible with the propene conversion requirement, and also the total target product selectivity ($S^{AC+AA}$ (mol %)) of the total desired product formation of acrolein (AC) and acrylic acid (AA) for the various all-active shaped catalyst bodies.

TABLE 3

| All-active shaped catalyst body | PSV (standard l/100 g · h) | $S^{AC+AA}$ (mol %) |
|---|---|---|
| E1 | 9 | 96.8 |
| E2 | 7 | 96.5 |
| E3 | 10 | 97.0 |
| E4 | 8.5 | 96.5 |
| C1 | 10 | 95.5 |
| C2 | 6 | 96.0 |
| C3 | 10 | 94.9 |
| C4 | 7 | 95.9 |
| C5 | 5.5 | 95.8 |
| C6 | 5 | 95.8 |
| C7 | 6 | 96.1 |

The results presented in table 3 clearly show that the examples (E) of all-active shaped catalyst bodies having a stoichiometry according to the invention of their multimetal oxide display better catalyst performance both in respect of the activity (higher space velocities of propene are compatible with the target conversion) and in respect of the total target product selectivity compared to the comparative (C) all-active shaped catalyst bodies.

The space velocity of propene PSV which is still compatible with a propene conversion target of 95 mol % at a bath temperature of 320° C. reflects the activity of the catalyst used. The higher "PSV", the higher the activity. The results reported in table 3 additionally demonstrate that an increased relative water content on mixing of aqueous solution A with aqueous solution B is advantageous both for the resulting activity and for the resulting total target product selectivity (E1 is better than E2; E3 is better than E4; C4 is better than C5; the multimetal oxides of the comparison pairings always have a uniform stoichiometry).

The U.S. provisional patent application No. 61/506,693, filed on Jul. 12, 2011, and No. 61/543,333, filed on Oct. 5, 2011, are incorporated by reference in the present application.

Numerous modifications and differences to/from the present application are possible in the light of the above-mentioned teachings. It can therefore be assumed that the invention, as defined in the attached claims, can be carried out in a manner other than that specifically described herein.

The invention claimed is:

1. An Mo-, Bi- and Fe-comprising multimetal oxide composition of the general stoichiometry I,

$$Mo_{12}Bi_aCo_bFe_cK_dSi_eO_x \qquad (I),$$

where the variables have the following meanings:
a=0.5 to 1,
b=7 to 8.5,
c=1.5 to 3.0,
d=0 to 0.15,
e=0 to 2.5 and x=a number which is determined by the valence and abundance of the elements other than oxygen in I and fulfil the following conditions:

$$12-b-1.5 \cdot c = A,$$

and

| 0.5 ≤ A ≤ 1.5; | condition 1 |
| 0.2 ≤ a/A ≤ 1.3; and | condition 2 |
| 2.5 ≤ b/c ≤ 9. | condition 3 |

2. The multimetal oxide composition according to claim 1 whose stoichiometric coefficient d is from 0.04 to 0.1.

3. The multimetal oxide composition according to any of claims 1 and 2 whose stoichiometric coefficient e is from 0.5 to 2.

4. The multimetal oxide composition according to claim 1, which fulfils the condition 1, 0.5 ≤ A ≤ 1.25.

5. The multimetal oxide composition according to claim 1, which fulfils the condition 2, 0.3 ≤ a/A ≤ 1.2.

6. The multimetal oxide composition according to claim 1, which fulfils the condition 3, 3 ≤ b/c ≤ 9.

7. A coated catalyst comprising a shaped support body and a coating of at least one multimetal oxide composition according to claim 1 present on the outer surface of the shaped support body.

8. An all-active shaped catalyst body whose active composition is at least one multimetal oxide according to claim 1.

9. The all-active shaped catalyst body according to claim 8 which has the geometry of a ring having a wall thickness of from 1 to 3 mm, a length of from 2 to 10 mm and an external diameter of from 2 to 10 mm.

10. A process for preparing a multimetal oxide composition according to claim 1, wherein a finely divided dry mix is produced from sources of elemental constituents of the multimetal oxide composition and this mixture is calcined at temperatures in the range from 350 to 650° C.

11. A process, comprising oxidizing an alkane, alkanol, alkanal, alkene and/or alkenal having from 3 to 6 carbon atoms over a catalyst bed, wherein the catalyst bed comprises at least one multimetal oxide composition according to claim 1.

12. The process according to claim 11, which is a process for the heterogeneously catalyzed partial gas-phase oxidation of propene to acrolein.

13. A process, comprising oxidizing an alkane, alkanol, alkanal, alkene and/or alkenal having from 3 to 6 carbon atoms over a catalyst bed, wherein the catalyst bed comprises at least one catalyst according to claim 7.

14. A process, comprising oxidizing an alkane, alkanol, alkanal, alkene and/or alkenal having from 3 to 6 carbon atoms over a catalyst bed, wherein the catalyst bed comprises at least one multimetal oxide composition obtained by the process according to claim 10.

* * * * *